(12) United States Patent
Achilefu et al.

(10) Patent No.: US 12,238,268 B2
(45) Date of Patent: *Feb. 25, 2025

(54) IMAGING SYSTEMS AND METHODS

(71) Applicant: Washington University, St. Louis, MO (US)

(72) Inventors: Samuel Achilefu, St. Louis, MO (US); Yang Liu, Akron, OH (US); Viktor Gruev, St. Louis, MO (US); Joseph P. Culver, Webster Groves, MO (US); Walter Akers, Columbia, IL (US); Adam Bauer, Webster Groves, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/448,547

(22) Filed: Aug. 11, 2023

(65) Prior Publication Data
US 2023/0388478 A1    Nov. 30, 2023

Related U.S. Application Data

(63) Continuation of application No. 17/689,339, filed on Mar. 8, 2022, now Pat. No. 11,765,340, which is a
(Continued)

(51) Int. Cl.
*G09G 5/00* (2006.01)
*A61B 34/00* (2016.01)
(Continued)

(52) U.S. Cl.
CPC ........... *H04N 13/344* (2018.05); *A61B 34/25* (2016.02); *A61B 90/30* (2016.02); *A61B 90/36* (2016.02);
(Continued)

(58) Field of Classification Search
CPC ................ A61B 1/0005; A61B 1/0692; A61B 2090/364; A61B 34/25; A61B 90/30;
(Continued)

(56) References Cited

U.S. PATENT DOCUMENTS

| 4,987,021 A | 1/1991 | Kanno |
| 5,107,063 A | 4/1992 | West |

(Continued)

FOREIGN PATENT DOCUMENTS

| JP | 06145539 | 5/1994 |
| WO | 1996017628 | 6/1996 |

(Continued)

OTHER PUBLICATIONS

Achilefu, S. et al., "Novel Receptor-Targeted Fluorescent Contrast Agents for In Vivo Tumor Imaging", Invest Radiol., 35(8):479-85, (2000).

(Continued)

*Primary Examiner* — Insa Sadio
(74) *Attorney, Agent, or Firm* — C A Schlecht; Midtown Intellectual Property, PC

(57) ABSTRACT

A goggle system is provided. The goggle system includes a computing device, a goggle device configured to be worn by a user and including a detector configured to simultaneously acquire image data of a subject in a first image mode and a second image mode, at least one eye assembly configured to display at least one of an image in the first image mode, an image in the second image mode, and a hybrid image including pixels of image data from the first image mode and pixels of image data from the second image mode, and a communications module configured to transmit acquired image data from the goggle device to the computing device.

20 Claims, 15 Drawing Sheets

Related U.S. Application Data continuation of application No. 17/122,848, filed on Dec. 15, 2020, now Pat. No. 11,310,485, which is a continuation of application No. 16/169,071, filed on Oct. 24, 2018, now Pat. No. 10,904,518, which is a continuation of application No. 14/374,002, filed as application No. PCT/US2013/022704 on Jan. 23, 2013, now Pat. No. 10,230,943.

(60) Provisional application No. 61/589,623, filed on Jan. 23, 2012.

(51) Int. Cl.
| | |
|---|---|
| *A61B 90/00* | (2016.01) |
| *A61B 90/30* | (2016.01) |
| *A61K 49/00* | (2006.01) |
| *C07K 7/06* | (2006.01) |
| *G02B 27/01* | (2006.01) |
| *H04N 13/344* | (2018.01) |
| *H04N 25/76* | (2023.01) |
| *A61B 1/00* | (2006.01) |
| *A61B 1/06* | (2006.01) |

(52) U.S. Cl.
CPC ........ *A61B 90/361* (2016.02); *A61K 49/0032* (2013.01); *A61K 49/0034* (2013.01); *A61K 49/0056* (2013.01); *C07K 7/06* (2013.01); *G02B 27/017* (2013.01); *H04N 25/76* (2023.01); *A61B 1/0005* (2013.01); *A61B 1/0692* (2013.01); *A61B 2090/364* (2016.02)

(58) Field of Classification Search
CPC .. A61B 90/36; A61B 90/361; A61K 49/0032; A61K 49/0034; A61K 49/0056; C07K 7/06; G02B 27/017; H04N 13/344; H04N 5/374
See application file for complete search history.

(56) References Cited

U.S. PATENT DOCUMENTS

| | | | |
|---|---|---|---|
| 5,254,852 A | 10/1993 | Filipovich |
| 5,268,486 A | 12/1993 | Waggoner |
| 5,290,670 A | 3/1994 | Delprato |
| 5,453,505 A | 9/1995 | Lee |
| 5,506,705 A | 4/1996 | Yamamoto |
| 5,508,161 A | 4/1996 | Miyake |
| 5,518,934 A | 5/1996 | Forrest |
| 5,589,250 A | 12/1996 | Asai |
| 5,955,224 A | 9/1999 | Caspar |
| 5,959,705 A | 9/1999 | Fergason |
| 5,972,890 A | 10/1999 | Lees |
| 6,027,709 A | 2/2000 | Little |
| 6,217,848 B1 | 4/2001 | Achilefu |
| 6,272,374 B1 | 8/2001 | Flock |
| 6,358,920 B1 | 3/2002 | Blaschuk |
| 6,487,428 B1 | 11/2002 | Culver |
| 6,491,894 B1 | 12/2002 | Ruoslahti |
| 6,554,444 B2 | 4/2003 | Shimada |
| 6,585,660 B2 | 7/2003 | Dorando |
| 6,610,651 B1 | 8/2003 | Ruoslahti |
| 6,652,835 B1 | 11/2003 | Lauffer |
| 6,747,159 B2 | 6/2004 | Caputo |
| 6,804,549 B2 | 10/2004 | Hayashi |
| 6,944,493 B2 | 9/2005 | Alam |
| 7,134,994 B2 | 11/2006 | Alpert |
| 7,172,907 B2 | 2/2007 | Chen |
| 7,211,778 B1 | 5/2007 | Smith |
| 7,547,721 B1 | 6/2009 | Miwa |
| 7,826,890 B1 | 11/2010 | Winchester, Jr. |
| 7,850,946 B2 | 12/2010 | Achilefu |
| 8,053,415 B2 | 11/2011 | Achilefu |
| 8,199,189 B2 | 6/2012 | Kagenow |
| 8,318,133 B2 | 11/2012 | Achilefu |
| 8,344,158 B2 | 1/2013 | Achilefu |
| 8,498,694 B2 | 7/2013 | Mcguire, Jr. |
| 8,556,820 B2 | 10/2013 | Alpert |
| 8,562,537 B2 | 10/2013 | Alpert |
| 8,586,924 B2 | 11/2013 | Demos |
| 8,636,659 B2 | 1/2014 | Alpert |
| 9,687,567 B2 | 6/2017 | Frangioni |
| 10,230,943 B2 | 3/2019 | Achilefu |
| 10,652,527 B2 | 5/2020 | Achilefu |
| 10,806,804 B2 | 10/2020 | Achilefu |
| 10,904,518 B2 | 1/2021 | Achilefu |
| 11,310,485 B2 | 4/2022 | Achilefu |
| 11,413,359 B2 | 8/2022 | Achilefu |
| 11,712,482 B2 | 8/2023 | Achilefu |
| 2002/0028474 A1 | 3/2002 | Shibamura |
| 2002/0030163 A1* | 3/2002 | Zhang ................ G02B 27/1066 |
| | | 348/E5.09 |
| 2002/0041898 A1 | 4/2002 | Unger |
| 2003/0105299 A1 | 6/2003 | Achilefu |
| 2004/0014981 A1 | 1/2004 | Lugade |
| 2004/0087778 A1 | 5/2004 | Feige |
| 2004/0215081 A1 | 10/2004 | Crane |
| 2006/0134001 A1* | 6/2006 | Frangioni ............ B82Y 30/00 |
| | | 424/9.6 |
| 2006/0173351 A1 | 8/2006 | Marcotte |
| 2006/0173360 A1 | 8/2006 | Kalafut |
| 2007/0042398 A1 | 2/2007 | Peng |
| 2007/0084985 A1 | 4/2007 | Smith |
| 2008/0204361 A1 | 8/2008 | Scales |
| 2009/0028788 A1 | 1/2009 | Achilefu |
| 2009/0074672 A1 | 3/2009 | Faris |
| 2009/0093761 A1 | 4/2009 | Sliwa |
| 2009/0124792 A1 | 5/2009 | Achilefu |
| 2009/0137908 A1 | 5/2009 | Patwardhan |
| 2009/0214436 A1 | 8/2009 | Achilefu |
| 2009/0234225 A1 | 9/2009 | Martin |
| 2009/0242797 A1 | 10/2009 | Yazdanfar |
| 2009/0268983 A1 | 10/2009 | Stone |
| 2010/0110308 A1 | 5/2010 | Nicholson |
| 2010/0113940 A1 | 5/2010 | Sen |
| 2010/0215585 A1 | 8/2010 | Frangioni |
| 2010/0240988 A1 | 9/2010 | Varga |
| 2010/0323389 A1 | 12/2010 | Xu |
| 2011/0123450 A1 | 5/2011 | Achilefu |
| 2011/0213625 A1 | 9/2011 | Joao |
| 2011/0297815 A1 | 12/2011 | Tian |
| 2012/0026308 A1 | 2/2012 | Johnson |
| 2013/0116403 A1 | 5/2013 | Achilefu |
| 2013/0129835 A1 | 5/2013 | Pollock |
| 2013/0175430 A1 | 7/2013 | Cunningham |
| 2013/0317368 A1 | 11/2013 | Warren |
| 2014/0023700 A1 | 1/2014 | Knudsen |
| 2014/0039309 A1 | 2/2014 | Harris |
| 2014/0046291 A1 | 2/2014 | Harris |
| 2014/0121475 A1 | 5/2014 | Alpert |
| 2014/0152467 A1 | 6/2014 | Spencer |
| 2014/0155753 A1 | 6/2014 | Mcguire, Jr. |
| 2014/0180032 A1 | 6/2014 | Millett |
| 2014/0180034 A1 | 6/2014 | Hoseit |
| 2014/0180056 A1 | 6/2014 | Hoseit |
| 2014/0180087 A1 | 6/2014 | Millett |
| 2014/0180135 A1 | 6/2014 | Hoseit |
| 2014/0180316 A1 | 6/2014 | Hoseit |
| 2014/0194704 A1 | 7/2014 | Millett |
| 2014/0200438 A1 | 7/2014 | Millett |
| 2014/0218210 A1 | 8/2014 | De Jong |
| 2014/0258743 A1 | 9/2014 | Nool |
| 2014/0275844 A1 | 9/2014 | Hoseit |
| 2014/0275950 A1 | 9/2014 | Hoseit |
| 2014/0276110 A1 | 9/2014 | Hoseit |
| 2015/0166791 A1 | 6/2015 | Achilefu |
| 2016/0206758 A1 | 7/2016 | Achilefu |
| 2016/0347727 A1 | 12/2016 | Frangioni |
| 2016/0370349 A1 | 12/2016 | Hoppin |
| 2018/0289842 A1 | 10/2018 | Achilefu |

(56) References Cited

U.S. PATENT DOCUMENTS

| | | | |
|---|---|---|---|
| 2022/0201274 | A1 | 6/2022 | Achilefu |
| 2022/0378950 | A1 | 12/2022 | Achilefu |
| 2023/0130831 | A1 | 4/2023 | Achilefu |

FOREIGN PATENT DOCUMENTS

| | | |
|---|---|---|
| WO | 1998022146 | 5/1998 |
| WO | 1998048838 | 11/1998 |
| WO | 1998048846 | 11/1998 |
| WO | 2000016810 | 3/2000 |
| WO | 2001005161 | 1/2001 |
| WO | 2001043781 | 6/2001 |
| WO | 2003074091 | 9/2003 |
| WO | 2004065491 | 8/2004 |
| WO | 2005000218 | 1/2005 |
| WO | 2006078914 | 7/2006 |
| WO | 2008017074 | 2/2008 |
| WO | 2011002209 | 1/2011 |
| WO | 2013112554 | 8/2013 |
| WO | 2016179350 | 11/2016 |
| WO | 2021119423 | 6/2021 |

OTHER PUBLICATIONS

Achilefu, S. et al., "Novel agent and system for imaging and therapy of arthritis", Washington University School of Medicine, 10 pages, (2021).

Achilefu, S. et al., "Synergistic Effects of Light-Emitting Probes and Peptides for Targeting and Monitoring Intergrin Expression", PNAS, 102(22):7976-81, (2005).

Achilefu, S. et al., "Synthesis, In Vitro Receptor Binding, and In Vivo Evaluation of Fluorescein and Carbocyanine Peptide-Based Contrast Agents", J Med Chem., 45(10):2003-15, (2002).

Achilefu, S., "Lighting up Tumors with Receptor-Specific Optical Molecular Probes", Technol Cancer Res Treat., 3(4):393-409, (2004).

Agrapidis-Paloympis, L et al., "The Effect of Solvents on the Ultraviolet Absorbance of Sunscreens", J Soc Cosmet Chem., 38:209-21, (1987).

Allman, R. et al., "In Vitro and in Vivo Effects of a Cyclic Peptide With Affinity for the alpha(nu) beta3 Integrin in Human Melanoma Cells", Eur J Cancer, 36(3):410-22, (2000).

Almutairi, K. et al., "The global prevalence of rheumatoid arthritis: a meta-analysis based on a systematic review", Rheumatol Int., 41(5):863-7, (2020).

Anonymous, "Guidelines for the management of rheumatoid arthritis. American College of Rheumatology Ad Hoc Committee on Clinical Guidelines", Arthritis Rheum., 39(5):713-22, (1996).

Arap, W. et al., "Cancer Treatment by Targeted Drug Delivery to Tumor Vasculature in a Mouse Model", Science, 279(5349):377-80, (1998).

Arnaout, M. et al., "Coming to Grips With Integrin Binding to Ligands", Curr Opin Biol., 14(5):641-51, (2002).

Arnaout, M., "Integrin Structure: New Twists and Turns in Dynamic Cell Adhesion", Immunol Rev., 186:125-40, (2002).

Bajpayee, A. et al., "Charge based intra-cartilage delivery of single dose dexamethasone using Avidin nano-carriers suppresses cytokine-induced catabolismlong term", Osteoarthritis Cartilage, 24(1):71-81, (2016).

Becker, A. et al., "Cyanine Dye Labeled Vasoactive Intestinal Peptide and Somaloslalin Analog for Optical Detection Jf Gastroenleropancreatic Tumors," Ann N Y Acad Sci., 291(1):275-8, (2000).

Becker, A. et al., "Receptor-Targeted Optical Imaging of Tumors With Near-Infrared Fluorescent Ligands", Nat Biotechnol., 19(4):327-31, (2001).

Becker, A. et al., "Transferrin-Mediated Tumor Delivery of Contrast Media for Optical Imaging and Magnetic Resonance Imaging", SPIE Confererence on Molecular Imaging: Reporters, Dyes, Markers and Instrumentation, 3600:142-50, (1999).

Berezin, M. et al., "Ratiometric Analysis of Fluorescence Lifetime for Probing Binding Sites in Albumin With Near-Infrared Fluorescent Molecular Probes", Photochem Photobiol., 83(6):1371-8, (2007).

Bharadwaj, A. et al., "Annexin A2 heterotetramer: structure and function", Int J Mol Sci., 14(3):6259-305, (2013).

Bhatnagar, S. et al., "Oral and Subcutaneous Administration of a Near-Infrared Fluorescent Molecular Imaging Agent Detects Inflammation in a Mouse Model of Rheumatoid Arthritis", Sci Rep., 9(1):4661, (2019).

Bloch, S. et al., "Targeting Beta-3 Integrin Using a Linear Hexapeptide Labeled with a Near-Infrared Fluorescent Molecular Probe", Mol Pharm., 3(5):539-49, (2006).

Bloch, S. et al., "Whole-Body Fluorescence Lifetime Imaging of a Tumor-Targeted Near-Infrared Molecular Probe in Mice", J Biomed Opt., 10(5):054003, (2005).

Bouteiller, C. et al., "Novel Water-Soluble Near-Infrared Cyanine Dyes: Synthesis, Spectral Properties, and Use in the Preparation of Internally Quenched Fluorescent Probes", Bioconjugate Chem., 18(4):1303-17, (2007).

Braeckmans, K. et al., "Three-dimensional Fluorescence Recovery After Photobleaching With the Confocal Scanning Laser Microscope", Biophys J., 85(4):2240-52, (2003).

Braga, J. et al., "Intracellular Macromolecular Mobility Measured by Fluorescence Recovery After Photobleaching With Confocal Laser Scanning Microscopes", Mol Biol Cell., 15(10):4749-60, (2004).

Bremer, C. et al., "Imaging of Differential Protease Expression in Breast Cancers for Detection of Aggressive Tumor Phenotypes", Radiology, 222(3):814-8, (2002).

Brinkley, M., "A Brief Survey of Methods for Preparing Protein Conjugates With Dyes, Haptens, and Cross-Linking Reagents", Bioconjug Chem., 3(1):2-13, (1992).

Bugaj, J. et al., "Novel Fluorescent Contrast Agents for Optical Imaging of in Vivo Tumors Based on a Receptor-Targeted Dye-Peptide Conjugate Platform", J Biomed Opt., 6(2):122-33, (2001).

Chen, W. et al., "Arthritis imaging using a near-infrared fluorescence folate-targeted probe", Arthritis Res Ther., 7(2):R310-7, (2005).

Chipon, B. et al., "Synthesis and Post-Synthetic Derivatization of a Cyanine-Based Amino Acid. Application to the Preparation of a Novel Water-Soluble NIR Dye", Tetrahedron Lett., 47(47):8279-84, (2006).

Cho, S. et al., "Indocyanine-Green for Fluorescence-Guided Surgery of Brain Tumors: Evidence, Techniques, and Practical Experience", Front Surg., 6(11):1-13, (2019).

Cooper, S., "Polyurethane Biomaterials", Abstract of Video Lecture; retrieved online at https://smartech.gatech.edu/handle/1853/42056, on Jul. 22, 2016; (2011).

De Jong, M. et al., "Comparison of 111 In-labeled Somatostatin Analogues for Tumor Scintigraphy and Radionuclide Therapy", Cancer Res., 58(3):437-41, (1998).

Definition of "Biomolecules," retrieved from https://www.thefreediclionary.com; 2 pages, (2014).

Deora, A. et al., "An annexin 2 phosphorylation switch mediates p11-dependent translocation of annexin 2 to the cell surface", J Biol Chem., 279(42):43411-8, (2004).

Deshpande, B. et al., "Number of Persons With Symptomatic Knee Osteoarthritis in the US: Impact of Race and Ethnicity, Age, Sex, and Obesity", Arthritis Care Res (Hoboken), 68(12):1743-50, (2016).

Enablement Decision Tree, accessed on Aug. 18, 2019, at URL: https://www.uspto.gov/web/offices/pac/dapp/1pecba.htm#7, Example F, situation 1.

EP Application No. 19152382.8; European Search Report, dated Sep. 18, 2019; 7 pages.

EP Patent Application No. 19152382.8; Extended European Search Report, dated Aug. 14, 2019; 7 pages.

Evans, C., "Catering to chondrocytes", Sci Transl Med., 10(469):eaav7043, (2018).

Fischer, T. et al., "Detection of rheumatoid arthritis using non-specific contrast enhanced fluorescence imaging", Acad Radiol., 17(3):375-81, (2010).

Fischer, T. et al., "Assessment of unspecific near-infrared dyes in laser-induced fluorescence imaging of experimental arthritis", Acad Radiol., 13(1):4-13, (2006).

(56) References Cited

OTHER PUBLICATIONS

Geiger, B. et al., "Cartilage-penetrating nanocarriers improve delivery and efficacy of growth factor treatment of osteoarthritis", Sci Transl Med., 10(469):eaat8800, (2018).
Glimm, A. et al., "Fluorescence optical imaging for treatment monitoring in patients with early and active rheumatoid arthritis in a 1-year follow-up period", Arthritis Res Ther., 21(1):209, (2019).
Gordon, G. et al., "Analysis of Simulated and Experimental Fluorescence Recovery After Photobleaching. Data for Two Diffusing Components", Biophys J., 68(3):766-78, (1995).
Grigor, C. et al., "Effect of a treatment strategy of tight control for rheumatoid arthritis (the TICORA study): a single-blind randomised controlled trial", Lancet., 364(9430):263-9, (2004).
Hansch, A. et al., "In vivo imaging of experimental arthritis with near-infrared fluorescence", Arthritis Rheum., 50(3):961-7, (2004).
Haraguchi, T., "Live Cell Imaging: Approaches for Studying Protein Dynamics in Living Cells," Cell Struct Funct., 27(5):333-4, (2002).
Haubner, R. et al., "Glycosylated RGD-containing Peptides: Tracer for Tumor Targeting and Angiogenesis Imaging With Improved Biokinetics", J Nucl Med., 42(2):326-36, (2001).
Haubner, R. et al., "Noninvasive Imaging of alpha(v)beta3 Integrin Expression Using 18F-labeled RGD-containing Glycopeptide and Positron Emission Tomography", Cancer Res., 61(5):1781-5, (2001).
Haubner, R. et al., "Radiolabeled alpha(v)beta3 Integrin Antagonists: A New Class of Tracers for Tumor Targeting", J Nucl Med., 40(6):1061-71, (1999).
Hilderbrand, S. et al., "Monofunctional Near-Infrared Fluorochromes for Imaging Applications," Bioconjug Chem., 16(5):1275-81, (2005).
Hunter, T. et al., "Prevalence of rheumatoid arthritis in the United States adult population in healthcare claims databases, 2004-2014", Rheumatol Int., 37(9):1551-7, (2017).
International Application No. PCT/US2004/017142; International Search Report and Written Opinion of the International Searching Authority, date of mailing Dec. 27, 2004; 6 pages.
International Application No. PCT/US2006/002056; International Preliminary Report on Patentability, date of issuance Jul. 24, 2007; 6 pages.
International Application No. PCT/US2006/002056; International Search Report and Written Opinion of the International Searching Authority, date of mailing May 24, 2006; 7 pages.
International Application No. PCT/US2013/022704; International Preliminary Report on Patentability, date of issuance Jul. 29, 2014; 5 pages.
International Application No. PCT/US2013/022704; International Search Report and Written Opinion of the International Searching Authority, date of mailing Apr. 18, 2013; 6 pages.
International Application No. PCT/US2016/030893; International Preliminary Report on Patentability, date of issuance Nov. 7, 2017; 9 pages.
International Application No. PCT/US2016/030893; International Search Report and Written Opinion of the International Searching Authority, date of mailing Sep. 9, 2016; 12 pages.
International Application No. PCT/US2020/064506; International Preliminary Report on Patentability, date of issuance Jun. 23, 2022; 7 pages.
International Application No. PCT/US2020/064506; International Search Report and Written Opinion of the International Searching Authority, date of mailing Apr. 22, 2021; 10 pages.
International Appliction No. PCT/US2006/002056; International Preliminary Report on Patentability, date of issuance Jul. 24, 2007; 7 pages.
Ito, S. et al., "Development of Fluorescence-Emitting Antibody Labeling Substance by Near-Infrared Ray Excitation", Bioorg Med Chem Lett., 5(22):2689-94, (1995).
Jain, R., "Barriers to Drug Delivery in Solid Tumors", Sci Am., 271(1):58-65, (1994).
Jamar, F. et al., "Scintigraphy using a technetium 99m-labelled anti-E-selectin Fab fragment in rheumatoid arthritis", Rheumatology (Oxford)., 41(1):53-61, (2002).

Janssen, M. et al., "Tumor Targeting With Radiolabeled alpha(v)beta(3) Integrin Binding Peptides in a Nude Mouse Model", Cancer Res., 62(21):6146-51, (2002).
Jones, J. et al., "Evaluation of a Tumor-Targeting, Near-Infrared Fluorescent Peptide for Early Detection and Endoscopic Resection of Polyps in a Rat Model of Colorectal Cancer", Mol Imaging, 17:1-9, (2018).
Kamradt, T. et al., "The role and clinical implications of G6PI in experimental models of rheumatoid arthritis", Arthritis Res Ther., 7(1):20-8, (2005).
Kisten, Y. et al., "Detection of clinically manifest and silent synovitis in the hands and wrists by fluorescence optical imaging", RMD Open., 1(1):e000106, (2015).
Krohn, M. et al., "Near-infrared Fluorescence Optical Imaging in Early Rheumatoid Arthritis: A Comparison to Magnetic Resonance Imaging and Ultrasonography", J Rheumatol., 42(7):1112-8, (2015).
Lee, H. et al., "Heptamethine Cyanine Dyes With a Robust C-C Bond at the Central Position of the Chromophore", J Org Chem., 71(20):7862-5, (2006).
Lee, H. et al., "Synthesis and Spectral Properties of Near-Infrared Aminophenyl-, Hydroxyphenyl-, and Phenyl-Substituted Heptamethine Cyanines", J Org Chem., 73(2):723-5, (2008).
Lenhard, J. et al., "Electrochemistry and Electronic Spectra of Cyanine Dye Radicals in Acetonitrile", J Phys Chem., 97(19):4916-25, (1993).
Leung, K.. "Cypate-Gly-Arg-Asp-Ser-Pro-Lys", Molecular Imaging and Contrast Agent Database (MICAD) [Internet]. Bethesda (MD): National Center for Biotechnology Information (US); 2004-13, (2005).
Lewis, J. et al., "Comparison of Four 64Cu-labeled Somatostatin Analogues in Vitro and in a Tumor-Bearing Rat Model: Evaluation of New Derivatives for Positron Emission Tomography Imaging and Targeted Radiotherapy", J Med Chem., 42(8):1341-7, (1999).
Lipsky, P. et al., "Infliximab and methotrexate in the treatment of rheumatoid arthritis. Anti-Tumor Necrosis Factor Trial in Rheumatoid Arthritis with Concomitant Therapy Study Group", N Engl J Med., 343(22):1594-602, (2000).
Liu, Y. et al., "Hands-Free, Wireless Goggles for Near-Infrared Fluorescence and Real-Time Image-Guided Surgery", Surgery, 149(5):689-98, (2011).
Licha, K. et al., "Hydrophilic Cyanine Dyes as Contrast Agents for Near-Infrared Tumor Imaging: Synthesis, Photophysical Properties and Spectroscopic in Vivo Characterization," Photochem Photobiol., 72(3):392-8, (2000).
Lukevits, É. et al., "Catalytic Synthesis and Reactions of Nitrogen Heterocycles (Review)", Chem Heterocyclic Compounds, 30(11-12):1284-307, (1994).
Meier, R. et al., "Indocyanine green-enhanced imaging of antigen-induced arthritis with an integrated optical imaging/radiography system", Arthritis Rheum., 62(8):2322-7, (2010).
Monach, P. et al., "The K/BxN arthritis model", Curr Protoc Immunol., Ch. 15, Un. 15.22, (2008).
Monach, P. et al., "The K/BxN mouse model of inflammatory arthritis: theory and practice", Methods Mol Med., 136:269-82, (2007).
Monti, S. et al., "Rheumatoid arthritis treatment: the earlier the better to prevent joint damage", RMD Open., 1(Suppl 1):e000057, (2015).
Mujumdar, R. et al., "Cyanine Dye Labeling Reagents: Sulfoindocyanine Succinimidyl Esters", Bioconjug Chem., 4(2):105-11, (1993).
National Institute of Cancer—Understanding and Related Topics, accessed Aug. 18, 2019 at URL: https://www.cancer.gov/about-cancer/understanding/what-is-cancer; 9 pages.
Ogul'Chansky, T. et al., "Interactions of Cyanine Dyes With Nucleic Acids. XXIV. Aggregation of Monomethine Cyanine Dyes in Presence of DNA and Its Manifestation in Absorption and Fluorescence Spectra ," Spectrochim Acta A Mol Biomol Spectrosc., 57(7):1525-32, (2001).
Otero, M. et al., "Cells of the synovium in rheumatoid arthritis. Chondrocytes", Arthritis Res Ther., 9(5):220, (2007).
Patonay, G. et al., "Near-Infrared Fluorogenic Labels: New Approach to an Old Problem", Anal Chem., 63(6):321A-7A, (1991).

(56) References Cited

OTHER PUBLICATIONS

Pretsch, E. et al., "UV-Absorption of alpha.beta-Unsaturated Carbonyl Compounds; UV-Absorption of Dienes and Polyenes; UV-Absorption of Aromatic Carbonyl Compounds; UV-Absorption of Aromatic Compounds," Spectral Data or Structure Determination of Organic Compounds, Chemical Laboratory Practice, 2nd ed., pp. U20, U25, U30, U35, U40, U45, U50, (1989).
Qin, R., "Intraoperative Fluorescence Surgical Goggle", Knowledge Bank OSU.EDU, 9 pages, (2009).
Registry No. 70446-35-4, 1 page, (1984).
Roland, J. et al., "Optical Versus Video See-Through Head-Mounted Displays in Medical Visualization", Presence, 9(3):287-309, (2000).
Romão, V. et al., "Major Challenges in Rheumatology: Will We Ever Treat Smarter, Instead of Just Harder?", Front Med (Lausanne), 6:144, (2019).
Rosner, B., "Fundamentals of Biostatistics", 7th ed. Boston: Brooks/Cole; (2011).
Salomon-Escoto, K. et al., "The 'Treat to Target' Approach to Rheumatoid Arthritis". Rheum Dis Clin North Am., 45(4):487-504, (2019).
Schäfer, V. et al., "Quantitative assessment of synovitis in patients with rheumatoid arthritis using fluorescence optical imaging.", Arthritis Res Ther., 15(5):R124, (2013).
Shen, D. et al., "Selective Imaging of Solid Tumours Via the Calcium-Dependent High-Affinity Binding of a Cyclic Octapeptide to Phosphorylated Annexin A2", Nat Biomed Engin., 4(3):298-313, (2020).
Sigma—® sodium dodecyl sulfate (Production Information), Product No. L 3771, retrieved from https://www.sigmaaldrich.com/content/dam/sigma-aldrich/docs/Sigma/Product_Information_Sheet/2/l3771 pis.pdf; 1 page, (revised Oct. 2002).
Sivolapenko, G. et al., "Imaging of Metastatic Melanoma Utilising a technetium-99m Labelled RGD-containing Synthetic Peptide", Eur J Nucl Med, 25(10): 1383-9, (1998).
Smolen, J. et al., "EULAR recommendations for the management of rheumatoid arthritis with synthetic and biological disease-modifying antirheumatic drugs: 2016 update", Ann Rheum Dis., 76(6):960-77, (2017).
Smolen, J. et al., "Tocilizumab inhibits progression of joint damage in rheumatoid arthritis irrespective of its anti-inflammatory effects: disassociation of the link between inflammation and destruction", Ann Rheum Dis., 71(5):687-93, (2012).
Song, C. et al., "Regulation of inflammatory response in human chondrocytes by lentiviral mediated RNA interference against S100A10", Inflamm Res., 61(11):1219-27, (2012).
Troyan, S. et al., "The FLARE Intraoperative Near-Infrared Fluorescence Imaging System: A First-in-Human Clinical Trial in Breast Cancer Sentinel Lymph Node Mapping", Ann Surg Oncol., 16(10):2943-52, (2009).
Tsen, S. et al., "Non-invasive monitoring of arthritis treatment response via targeting of tyrosine- phosphorylated annexin A2 in chondrocytes", Arthritis Res Ther., 23(1):265, (2021).
Tseng, C. et al., "Dual Role of Chondrocytes in Rheumatoid Arthritis: The Chicken and the Egg", Int J Mol Sci., 21(3):1071, (2020).
U.S. Appl. No. 10/559,000; Notice of Allowance, dated Aug. 2, 2010; 4 pages.
U.S. Appl. No. 10/559,000; Final Office Action, dated Oct. 14, 2009; 10 pages.
U.S. Appl. No. 10/559,000; Non-Final Office Action, dated Mar. 3, 2010; 4 pages.
U.S. Appl. No. 10/559,000; Non-Final Office Action, dated Mar. 10, 2009; 8 pages.
U.S. Appl. No. 12/192,480; Final Office Action, dated Dec. 13, 2011; 9 pages.
U.S. Appl. No. 12/192,480; Non-Final Office Action, dated Aug. 19, 2011; 10 pages.
U.S. Appl. No. 12/192,480; Non-Final Office Action, dated Mar. 7, 2011; 13 pages.
U.S. Appl. No. 12/192,480; Non-Final Office Action, dated May 1, 2012; 12 pages.
U.S. Appl. No. 12/192,480; Notice of Allowance, dated Sep. 4, 2012; 7 pages.
U.S. Appl. No. 12/370,758; Final Office Action, dated May 25, 2012; 12 pages.
U.S. Appl. No. 12/370,758; Non-Final Office Action, dated Aug. 28, 2014; 10 pages.
U.S. Appl. No. 12/370,758; Non-Final Office Action, dated Dec. 4, 2015; 10 pages.
U.S. Appl. No. 12/370,758; Non-Final Office Action, dated Sep. 30, 2011; 12 pages.
U.S. Appl. No. 12/938,086; Non-Final Office Action, dated Apr. 3, 2012; 8 pages.
U.S. Appl. No. 12/938,086; Notice of Allowance, dated Jul. 23, 2012; 7 pages.
U.S. Appl. No. 13/712,317; Final Office Action, dated Jul. 11, 2014; 12 pages.
U.S. Appl. No. 13/712,317; Non-Final Office Action, dated Jan. 17, 2014; 15 pages.
U.S. Appl. No. 13/712,317; Non-Final Office Action, dated May 21, 2015; 14 pages.
U.S. Appl. No. 14/624,532; Final Office Action, dated Dec. 1, 2017; 8 pages.
U.S. Appl. No. 14/624,532; Final Office Action, dated Nov. 4, 2016; 11 pages.
U.S. Appl. No. 14/624,532; Non-Final Office Action, dated Jul. 5, 2017; 9 pages.
U.S. Appl. No. 14/624,532; Non-Final Office Action, dated Jul. 15, 2016; 12 pages.
U.S. Appl. No. 15/090,055; Final Office Action, dated Aug. 9, 2019; 9 pages.
U.S. Appl. No. 15/090,055; Final Office Action, dated Jul. 24, 2017; 16 pages.
U.S. Appl. No. 15/090,055; Non-Final Office Action, dated Apr. 6, 2017; 17 pages.
U.S. Appl. No. 15/090,055; Non-Final Office Action, dated Nov. 7, 2018; 10 pages.
U.S. Appl. No. 15/572,087; Final Office Action, dated Jan. 17, 2020; 25 pages.
U.S. Appl. No. 15/572,087; Notice of Allowance, dated Jun. 10, 2020; 11 pages.
U.S. Appl. No. 16/169,071; Applicant-Initiated Interview Summary, dated Jul. 2, 2020; 3 pages.
U.S. Appl. No. 16/169,071; Applicant-Initiated Interview Summary, dated Sep. 18, 2020; 2 pgaes.
U.S. Appl. No. 16/169,071; Corrected Notice of Allowability, dated Dec. 17, 2020; 4 pages.
U.S. Appl. No. 16/169,071; Final Office Action, dated Jun. 26, 2020; 13 pages.
U.S. Appl. No. 16/169,071; Notice of Allowance, dated Sep. 28, 2020; 8 pages.
U.S. Appl. No. 16/189,551; Notice of Allowance, dated Jan. 20, 2020; 5 pages.
U.S. Appl. No. 17/017,135; Examiner-Initiated Interview Summary, dated May 6, 2022; 1 page.
U.S. Appl. No. 17/017,135; Non-Final Office Action, dated Dec. 22, 2021; 25 pages.
U.S. Appl. No. 17/017,135; Notice of Allowance, dated May 12, 2022; 10 pages.
U.S. Appl. No. 17/119,305; Notice of Allowance, dated Mar. 3, 2023; 11 pages.
U.S. Appl. No. 17/122,848; Non-Final Office Action, dated Aug. 11, 2021; 22 pages.
U.S. Appl. No. 17/122,848; Notice of Allowance, dated Dec. 15, 2021; 5 pages.
U.S. Appl. No. 17/689,339; Non-Final Office Action, dated Jan. 25, 2023; 25 pages.
U.S. Appl. No. 17/689,339; Notice of Allowance, dated May 15, 2023; 11 pages.
Van Hagen, P. et al., "Evaluation of a Radiolabelled Cyclic DTPA-RGD Analogue for Tumour Imaging and Radionuclide Therapy", Int J Cancer, 90(4): 186-98, (2000).

(56) References Cited

OTHER PUBLICATIONS

Viitanen, R. et al., "First-in-Humans Study of 68Ga-DOTA-Siglec-9, a PET Ligand Targeting Vascular Adhesion Protein 1", J Nucl Med., 62(4):577-83, (2021).
Vina, E. et al., "Epidemiology of osteoarthritis: literature update", Curr Opin Rheumatol., 30(2):160-7, (2018).
Wakefield, R. et al., "The value of sonography in the detection of bone erosions in patients with rheumatoid arthritis: a comparison with conventional radiography", Arthritis Rheum., 43(12):2762-70, (2000).
Wang, H. et al., "Indocyanine green-incorporating nanoparticles for cancer theranostics", Theranostics, 8(5):1227-42, (2018).
Weissleder, R., "A Clearer Vision for in Vivo Imaging ," Nat Biotechnol., 19(4):316-7, (2001).
Werle, M. et al., "Strategies to improve plasma half life time of peptide and protein drugs", Amino Acids, 30(4):351-67, (2006).
Werner, S. et al., "Indocyanine green-enhanced fluorescence optical imaging in patients with early and very early arthritis: a comparative study with magnetic resonance imaging", Arthritis Rheum., 65(12):3036-44, (2013).
Werner, S. et al., "Inflammation assessment in patients with arthritis using a novel in vivo fluorescence optical imaging technology", Ann Rheum Dis., 71(4):504-10, (2012).
Wijbrandts, C. et al., "Prediction of Response to Targeted Treatment in Rheumatoid Arthritis", Mayo Clin Proc., 92(7):1129-43, (2017).
Yang, L. et al., "Hands-Free, Wireless Goggles for Near-Infrared Fluorescence and Real-Time Image-Guided Surgery", Surgery, 149(5):689-98, (2011).
Ye, Y. et al., "Design, Synthesis, and Evaluation of Near Infrared Fluorescent Multimeric RGD Peptides for Targeting Tumors ", J Med Chem., 49(7):2268-75, (2006).
Ye, Y. et al., "Integrin Targeting for Tumor Optical Imaging", Theranostics, 1:102-26, (2011).
Ye, Y. et al., "Multivalent Carbocyanine Molecular Probes: Synthesis and Applications", Bioconjug Chem, 16(1):51-61, (2005).
Ye, Y. et al., "Novel Near-Infrared Fluorescent Integrin-Targeted DFO Analogue", Bioconjug Chem., 19(1):225-34, (2008).
Ye, Y. et al., "Polyvalent Carbocyanine Molecular Beacons for Molecular Recognitions", J Am Chem, 126(25):7740-1, (2004).
Yi, J. et al., "The Annexin a2 Promotes Development in Arthritis through Neovascularization by Amplification Hedgehog Pathway", PLoS One, 11(3):e0150363, (2016).
Zhang, Z. et al., "Monomolecular Multimodal Fluorescence-Radioisotope Imaging Agents", Bioconjug Chem., 16(5):1232-9, (2005).
Zhao, W. et al., "The discoidin domain receptor 2/annexin A2/matrix metalloproteinase 13 loop promotes joint destruction in arthritis through promoting migration and invasion of fibroblast-like synoviocytes", Arthritis Rheumatol., 66(9):2355-67, (2014).
Zheng, L. et al., "Tyrosine 23 phosphorylation-dependent cell-surface localization of annexin A2 is required for invasion and metastases of pancreatic cancer", PLoS One., 6(4):e19390, (2011).
Zhou, H. et al., "Alphavbeta3-targeted nanotherapy suppresses inflammatory arthritis in mice", FASEB J., 23(9):2978-85, (2009).
Zhou, H. et al., "Synergistic effect of antiangiogenic nanotherapy combined with methotrexate in the treatment of experimental inflammatory arthritis", Nanomedicine (Lond)., 5(7):1065-74, (2010).
Charanya, T., York, T., Bloch, S., Sudlow, G., Liang, K., Garcia, M., Akers, W.J., Rubin, D., Gruev, V. and Achilefu, S., 2014. Trimodal color-fluorescence-polarization endoscopy aided by a tumor selective molecular probe accurately detects flat lesions in colitis-associated cancer. Journal of biomedical optics, 19(12), pp. 126002-126002.

* cited by examiner

IMAGING SYSTEMS AND METHODS

CROSS REFERENCE TO RELATED APPLICATIONS

This application is a continuation of U.S. patent application Ser. No. 17/689,339 filed Mar. 8, 2022, now allowed, which is a continuation of U.S. patent application Ser. No. 17/122,848 filed Dec. 15, 2020, now U.S. Pat. No. 11,310,485, which is a continuation of U.S. patent application Ser. No. 16/169,071 filed Oct. 24, 2018, now U.S. Pat. No. 10,904,518, which is a continuation of U.S. patent application Ser. No. 14/374,002 filed Jul. 23, 2014, now U.S. Pat. No. 10,230,943, which is a National Stage Entry of PCT/US2013/022704 filed Jan. 23, 2013, which claims priority from U.S. Provisional Application No. 61/589,623 filed Jan. 23, 2012, all of which are incorporated herein in their entireties.

STATEMENT REGARDING FEDERALLY SPONSORED RESEARCH OR DEVELOPMENT

This invention was made with government support under grant numbers EB008111 and EB008458 awarded by the National Institutes of Health. The government has certain rights in the invention.

BACKGROUND

The field of the disclosure generally relates to imaging systems and methods, and more specifically, to goggles for displaying a plurality of image modes.

For surgical operations, in the absence of an image guidance system, surgeons typically need to remove large surgical margins around what they perceive as a neoplastic tissue because of the similarity of diseased tissue to surrounding healthy tissue. In some parts of the body, such as the brain, surgeons do not have the luxury of removing sizeable healthy tissue for fear of inducing irreparable damage. Despite progress made to enhance the contrast between neoplastic and normal tissues, the human eye is not capable of detecting the contrast signals with high sensitivity in the operating room. This limitation exasperates tumor resection, resulting in the presence of cancerous cells at or near the boundaries of surgically removed tissues.

Recent advances in medical imaging technologies, however, have facilitated the use of imaging instruments to guide surgical resections. However, at least some known imaging systems have relatively low sensitivity and accuracy. Further, at least some known imaging systems generally require high costs, complex instrumentation, and time-consuming image analysis. Moreover, some surgical procedures often require a team of experienced oncologic surgeons, radiologists, and pathologists to work together. Finally, at least some known imaging systems include a graphic display of results on a monitor, which can distract surgeons from focusing on the surgery at hand.

SUMMARY

In one aspect, a goggle system is provided. The goggle system includes a computing device, a goggle device configured to be worn by a user and including a detector configured to simultaneously acquire image data of a subject in a first image mode and a second image mode, at least one eye assembly configured to display at least one of an image in the first image mode, an image in the second image mode, and a hybrid image including pixels of image data from the first image mode and pixels of image data from the second image mode, and a communications module configured to transmit acquired image data from the goggle device to the computing device.

In another aspect, a goggle device configured to be worn by a user is provided. The goggle device includes a detector configured to simultaneously acquire image data of a subject in a first image mode and a second image mode, and at least one eye assembly configured to display at least one of an image in the first image mode, an image in the second image mode, and a hybrid image including pixels of image data from the first image mode and pixels of image data from the second image mode.

In yet another aspect, a method for assembling a goggle device is provided. The method includes providing a detector configured to simultaneously acquire image data of a subject in a first image mode and a second image mode, coupling at least one eye assembly to the detector such that the at least one eye assembly is configured to display at least one of an image in the first image mode, an image in the second image mode, and a hybrid image including pixels of image data from the first image mode and pixels of image data from the second image mode, and coupling a fastening device to the at least one eye assembly, the fastening device configured to secure the goggle device to a user.

In yet another aspect, a goggle device for fluorescence imaging configured to be worn by a user is provided. The goggle device includes a head-mounted display configured to switch between optical see-through and video see-through modes, a complementary metal-oxide-semiconductor (CMOS) imaging sensor, and a control module configured to interface between the CMOS imaging sensor and a computing device.

In yet another aspect, a method for fluorescence imaging is provided. The method includes administering a fluorescent molecular probe to a subject, observing the subject using a goggle device configured for at least one of visible light and near infrared light imaging, and identifying, using the goggle device, at least one tumor in the subject based on binding of the fluorescent molecular probe to tissue.

BRIEF DESCRIPTION OF THE DRAWINGS

The embodiments described herein may be better understood by referring to the following description in conjunction with the accompanying drawings.

DETAILED DESCRIPTION

Embodiments described herein provide a goggle system that includes a goggle device in communication with a computing device. The goggle device enables a user to view a subject in a plurality of imaging modes in real-time. The imaging modes include a hybrid-imaging mode that simultaneously displays pixels of image data of a first imaging mode and pixels of image data of a second imaging mode. Accordingly, a user is able to quickly and easily visualize a subject during a surgical operation.

Figure 1:
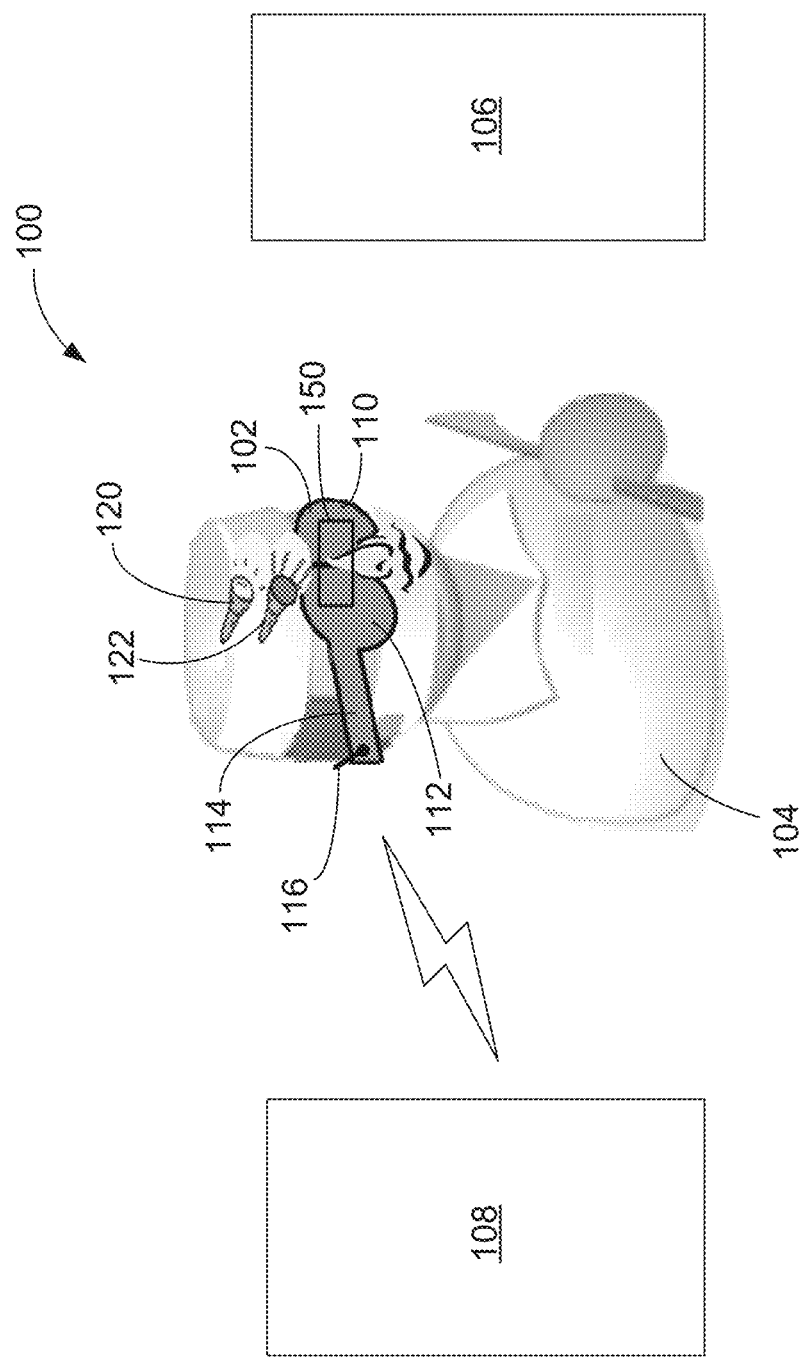
FIG. 1 is a schematic diagram of an exemplary goggle system.
Figure 2:
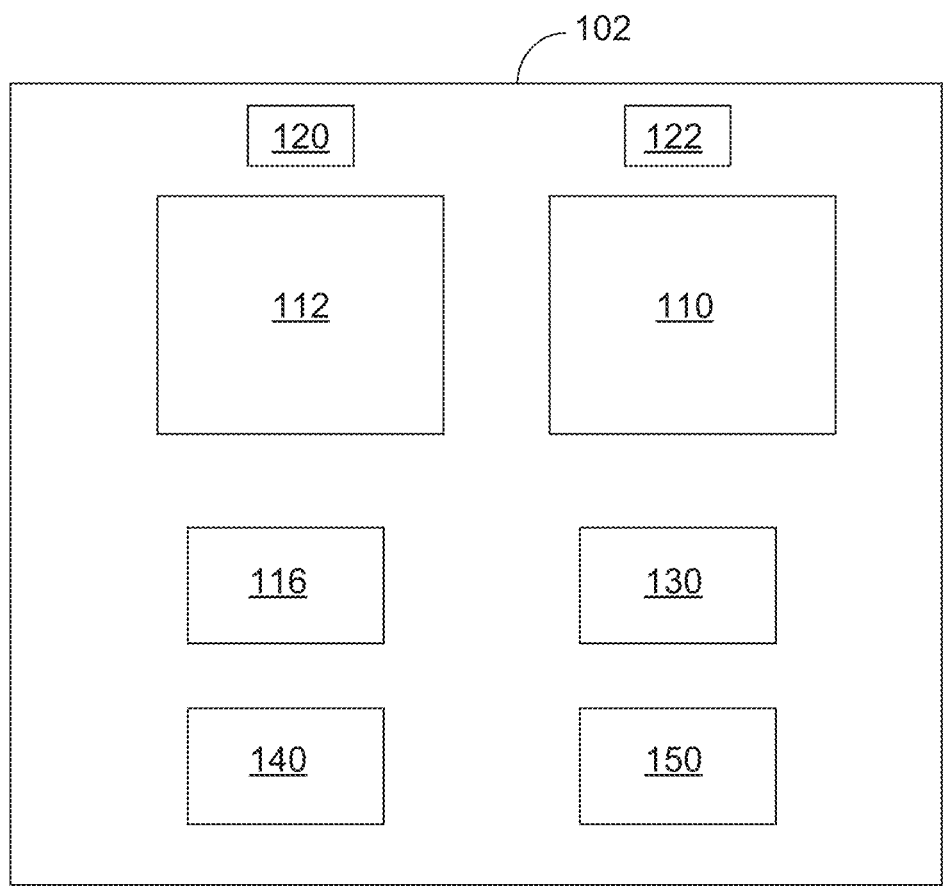
FIG. 2 is a block diagram of the goggle device shown in FIG. 1.

FIG. 1 is a schematic diagram of an exemplary goggle system 100. FIG. 2 is a block diagram of a goggle device 102 that may be used with goggle system 100. Goggle device 102 may be worn by a user 104, such as a surgeon, and aids user 104 in viewing a subject 106, as described in detail herein. In the exemplary embodiment, goggle device 102 transmits and/or receives data from a computing device 108. Data may be transferred between computing device 108 and goggle device 102 over a wired or wireless network.

In the exemplary embodiment, goggle device 102 includes a left eye assembly 110 that displays an image for a left eye of user 104, and a right eye assembly 112 that displays an image for a right eye of user 104. Goggle device 102 further includes a fastening device 114, such as a strap, for securing goggle device 102 to user 104 during use.

Goggle device 102 enables user 104 to view subject 106 in a plurality of image modes. In the exemplary embodiment, goggle device 102 enables user 104 to view a far- or near-infrared (NIR) image of subject 106, a visible light image of subject 106, and a hybrid near-infrared/visible light image of subject 106. Alternatively, goggle device 102 may enable user 104 to view a subject in any image mode and/or combination of image modes, including, for example, photoacoustic images, interference images, optical coherence tomography images, diffusion optical tomography images, polarization images, ultrasound images, magnetic resonance imaging (MRI) images, nuclear images (e.g., positron emission tomography (PET) images, single-photon emission computed tomography (SPECT) images), computed tomography (CT) images, gamma-imaging, and X-ray images.

A switch 116 on goggle device 102 enables user 104 to switch between image modes. In the exemplary embodiment, switch 116 is a toggle switch. Alternatively, switch 116 may be any type of switching device that enables goggle device 102 to function as described herein. For example, in one embodiment, switch 116 is a foot pedal, and user 104 activates switch 116 by depressing the foot pedal. In another embodiment, switch 116 is voice-activated.

Switch 116 controls which image mode is displayed on left eye assembly 110 and right eye assembly 112. In the exemplary embodiment, switch 116 controls whether left eye assembly 110 and/or right eye 112 assembly displays a visible light image, a near-infrared image, or a hybrid near-infrared/visible light image. In one embodiment, left eye assembly 110 and right eye assembly 112 each have a respective switch 116. Accordingly, in some embodiments, user 104 may view a first image mode on left eye assembly 110 and a second image mode on right eye assembly 112.

Goggle device 102 further includes sources for imaging. In one embodiment, the goggle device includes a white light (i.e., visible light) source 120 and a near-infrared light source 122. White light source 120 and near-infrared light source 122 illuminate subject 106 with visible light and near-infrared light, respectively. In other embodiments, different light sources may be utilized for different specific imaging modes. For example, suitable light sources may be integrated with goggle device 102 to enable the capture of photoacoustic images, interference images, optical coherence tomography images, diffusion optical tomography images, polarization images, far infrared images, thermal images, ultrasound images, and nuclear images (e.g., PET, SPECT, CT, gamma-imaging, X-ray).

In the exemplary embodiment, white light source 120 includes a plurality of white light-emitting diodes (LEDs), and near-infrared light source 122 includes a plurality of near-infrared LEDs for fluorescence imaging. White light source 120 and near-infrared light source 122 each provide a field of view of approximately 0.3 m in diameter at 1.0 m from the respective source. Alternatively, white light source 120 and near-infrared light source 122, including any components that enable goggle device 102 to function as described herein, such as, for example, laser, laser diodes, light bulbs, or any combination of the aforementioned components. Alternatively, near-infrared light source 122 may include light sources in other wavelengths to enable absorption or luminescence, or fluorescence imaging in other spectral windows.

Near-infrared light emitted from near-infrared light source 122 excites fluorescent molecular probes present in subject 106. For example, for a tumor resection operation, a molecular probe capable of fluorescent excitation is injected into a subject. The molecular probe includes a peptide sequence and a near-infrared fluorescent dye, such as indocyanine green dye, having absorption and emission maxima around 780 nm and 830 nm, respectively. After injecting the molecular probe into the subject 106, the molecular probe binds to tumors. Accordingly, when near-infrared light from near-infrared light source 122 strikes subject 106, the fluorescent dye in the molecular probe is excited. With the fluorescent dye excited, lesions such as tumors can quickly and easily be visualized in the near-infrared imaging mode of goggle device 102. A similar procedure is applicable in other spectral regions.

To transfer data between goggle device 102 and one or more remote devices, such as computing device 108, the goggle device includes a communications module 130. In the exemplary embodiment, for transfer of data over a wireless network, communications module 130 includes a radio-frequency (RF) transmitter/receiver. Data transfer can also be accomplished through other suitable platforms such as, for example, Bluetooth, WI-FI, infrared (IR) communication, internet, 3G, 4G network, satellite, etc. Communications module 130 may also be transfer data to computing device 108 over a wired connection, such as for example, a USB video capture cable. Communications module 130 enables image data collected by goggles to be displayed and/or stored on computing device 108. Accordingly, image data acquired by goggle device 102 can be viewed not only on goggle device 102 but also on computing device 108.

Goggle device 102 includes a power module 140 that supplies power to goggle device 102. In the exemplary embodiment, power module 140 is a battery unit that stores and provides electrical energy to goggle device 102. Alternatively, power module 140 is any device configured to supply power to goggle device 102.

To acquire image data of subject 106 to display on left eye assembly 110 and right eye assembly 112, goggle device 102 includes a detector module 150. In the exemplary embodiment, detector module 150 is a hybrid detector array capable of detecting both near-infrared and visible light. Detector module 150 is mounted on the front of goggle device 102 to collect image data from a direction that user 104 is facing. Detector module 150 displays received image data on left eye assembly 110 and right eye assembly 112 such that left eye assembly 110 and right eye assembly 112 display the same regions of subject 106 that a left eye and right eye of user 104 would observe in the absence of goggle device 102.

Figure 3:
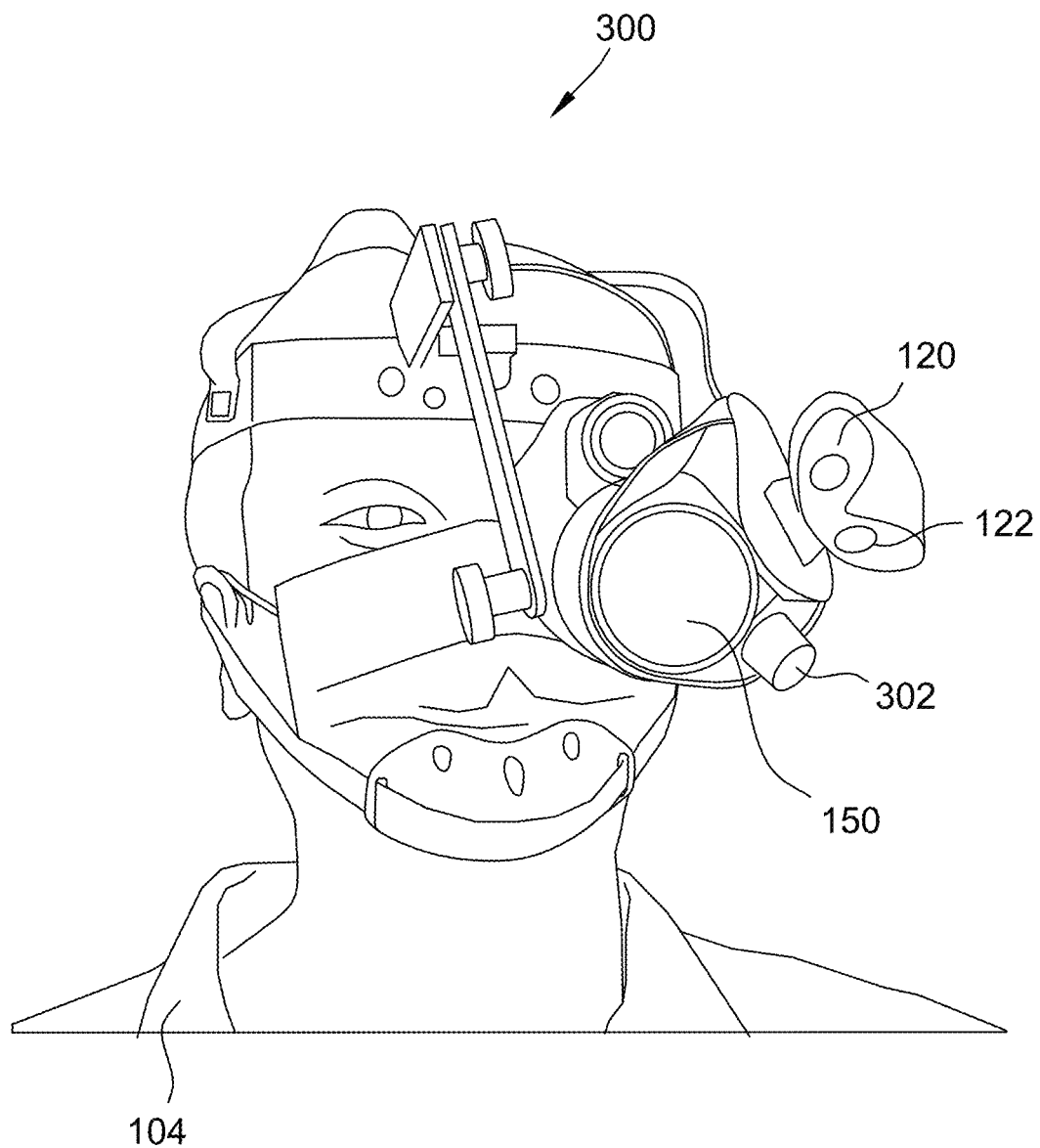
FIG. 3 is an image of an alternative goggle device.

FIG. 3 is an image of an alternative goggle device 300 that may be used with goggle system 100 (shown in FIG. 1). Goggle device 300 includes components substantially similar to goggle device 102, and like reference numerals are used herein to identify like components. Unlike goggle device 102, goggle device 300 includes only a single eye assembly 302. As such, when using goggle device 300, one eye of user 104 views subject 106 through single eye assembly 302, and the other eye of user 104 views subject uninhibited (i.e., with the naked eye).

Single eye assembly 302 functions substantially similar to left eye assembly 110 and right eye assembly 112 (shown in FIGS. 1 and 2). In the exemplary embodiment, single eye assembly 302 covers the left eye of user 104. Alternatively, single eye assembly 302 may cover the right eye of user 104.

Figure 4:
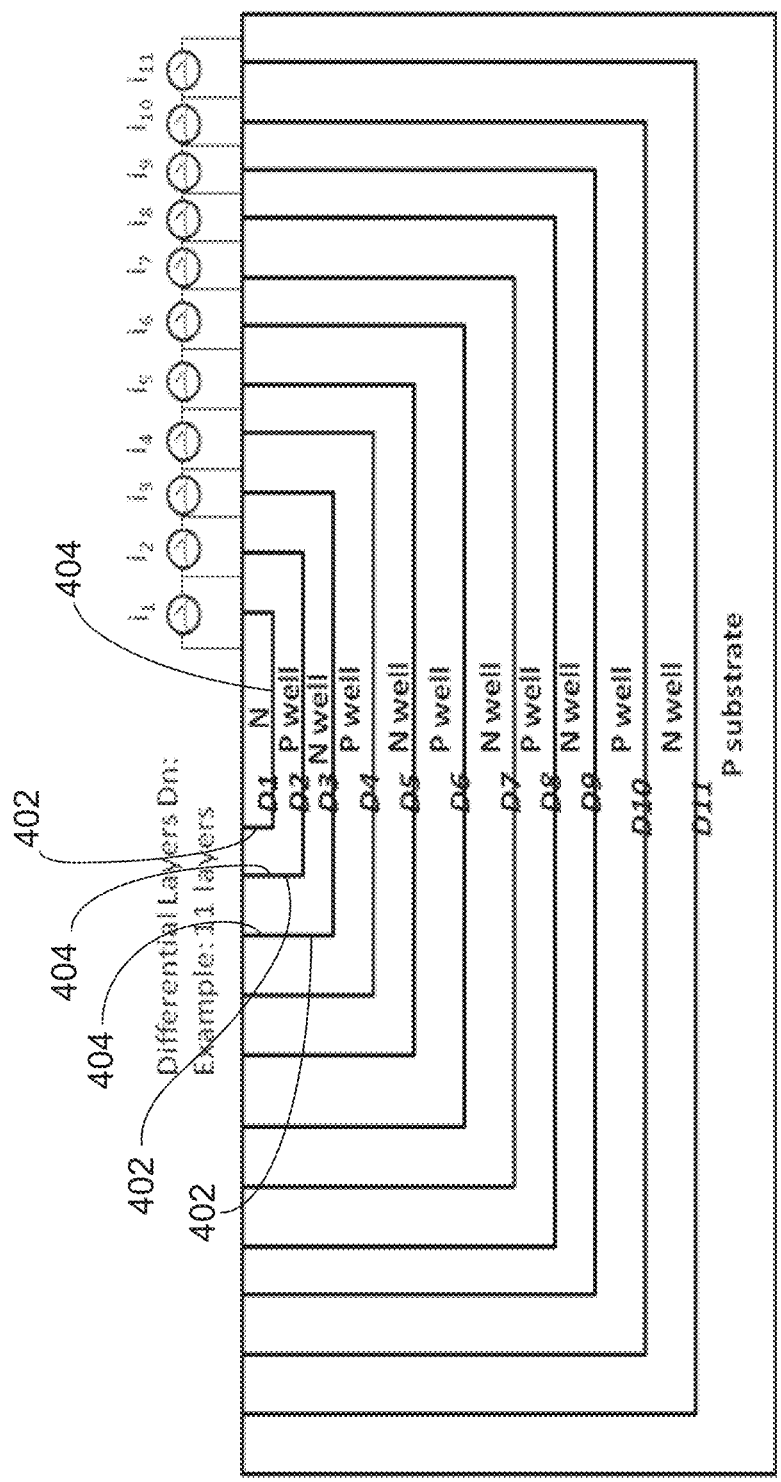
FIG. 4 is a schematic diagram of an exemplary detector element that may be used with the goggle device shown in FIG. 1.

FIG. 4 is a schematic diagram of a detector element 400 that may be used with detector module 150 to collect image data for goggle device 102 (both shown in FIGS. 1 and 2). Detector element 400 includes a plurality of differential layers 402 (denoted by Dn) along a differential length in a continuum. In the exemplary embodiment, each differential layer 402 is a p-n junction 404. In the exemplary embodiment, detector element 400 includes eleven differential layers 402. Alternatively, detector element 400 may include any number of differential layers 402 that enables detector element 400 to function as described herein. The longer the wavelength of the incident light, the deeper the light will penetrate detector element 400. Accordingly, each layer 402 is configured to detect a different frequency range of incident light. For example, in one embodiment, channels D5-D8 detect blue light (i.e., light with a wavelength of approximately 440-490 nm), and the total wavelength spectrum detectable by detector element 400 is less than 300 nm to greater than 1300 nm. By using a continuum of differential layers 402, detector element 400 is capable of simultaneously detecting a broad range of wavelengths of the incident light, including visible light (i.e., red, green, and blue light), near-infrared light, and various other wavelengths.

Images can be generated from the image data acquired by a selection of differential layers 402. For example, to generate a visible light image, image data from differential layers 402 corresponding to red, blue, and green light is used. Further, images may be generated using addition, subtraction, integration, differentiation, and/or thresholding of differential layers 402. Accordingly, image data acquired using detector element 400 may be used to generate a variety of images.

Figure 5:
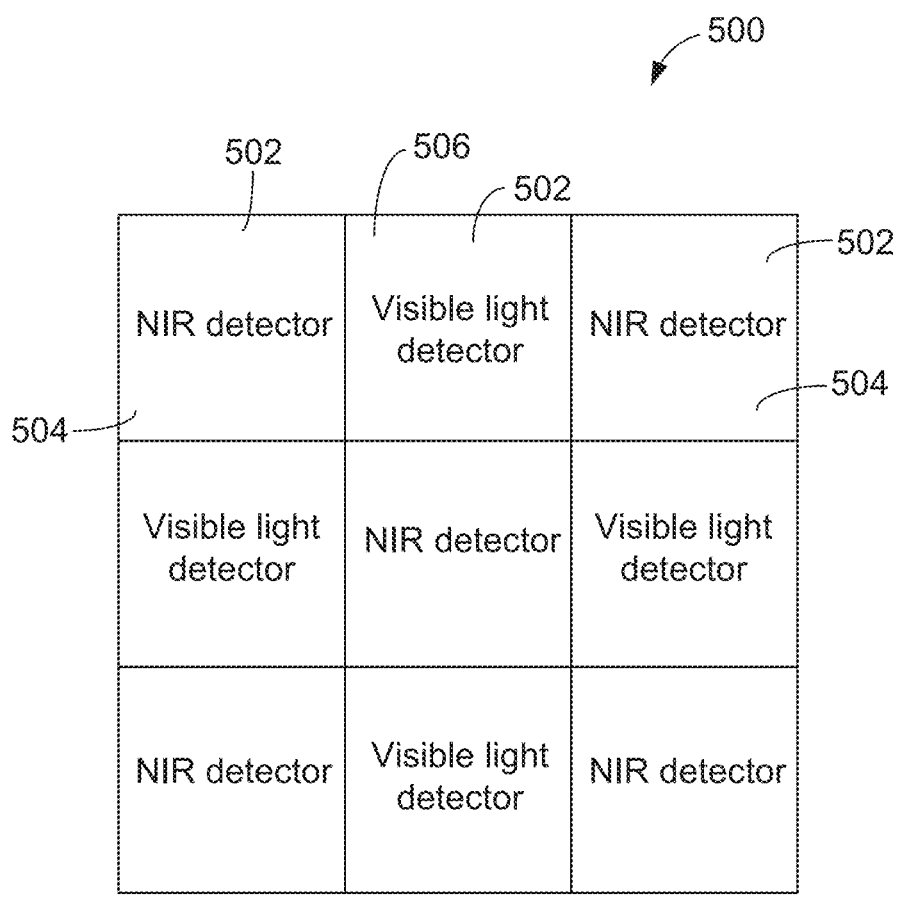
FIG. 5 is a schematic diagram of a portion of an exemplary detector array that may be used with the goggle device shown in FIG. 1.

FIG. 5 is a schematic diagram of a portion of a detector array 500 that may be used with detector module 150 (shown in FIG. 2). Detector array 500 includes a plurality of detector elements 502. In some embodiments, each detector element 502 corresponds to one pixel. In the exemplary embodiment, array 500 includes near-infrared detector elements 504 and visible light detector elements 506 arranged in a checkerboard pattern. That is, near-infrared detector elements 504 and visible light detector elements 506 alternate in both a horizontal and vertical direction. Notably, this concept is not restricted to near-infrared detector elements or visible pixel elements. That is, for different imaging applications, near-infrared detector elements 504 and/or visible pixel detector elements 506 may be replaced detector elements in other wavelength windows, such as, for example, 500 nm-550 nm, 600 nm-630 nm, 1100 nm-1150 nm, 1200 nm-1300 nm, etc.

In the exemplary embodiment, visible light detector elements 506 are continuum detector elements, such as detector element 400 (shown in FIG. 4), and near-infrared detector elements 504 are single-channel detector elements. Alternatively, visible light detector elements 506 and near-infrared detector elements 504 may be any type of detector element that enables detector array 500 to function as described herein.

Figure 6:
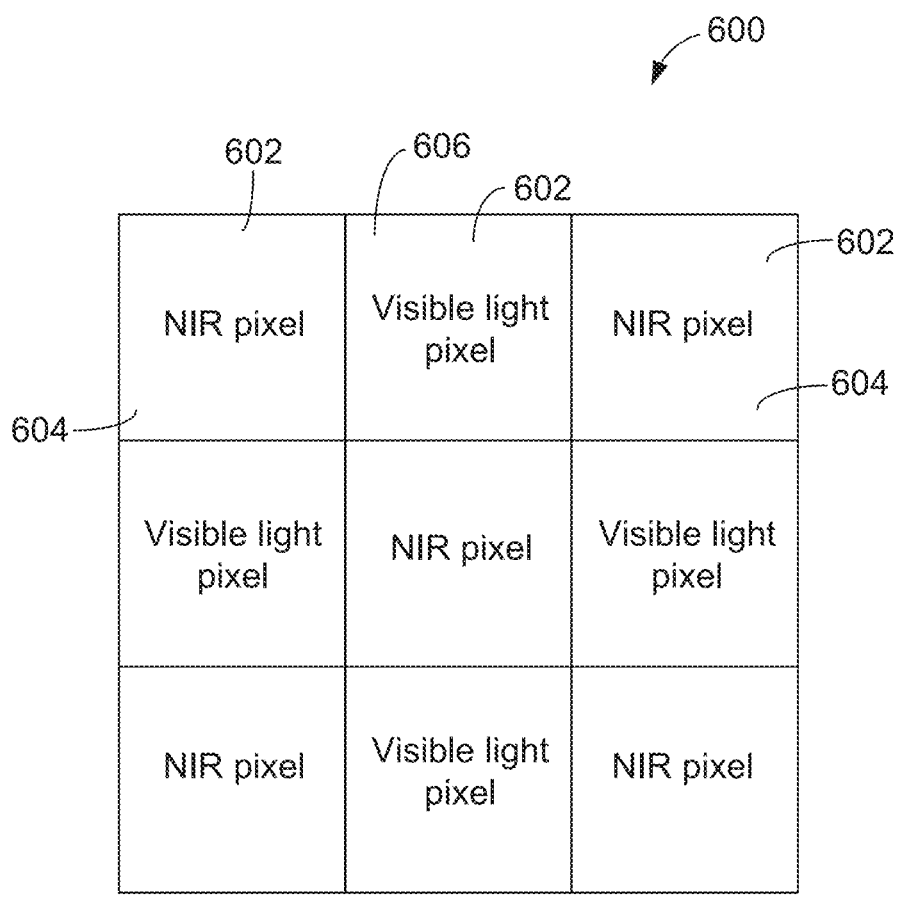
FIG. 6 is a schematic diagram of a portion of an exemplary pixel array that may be used with the goggle device shown in FIG. 1.

FIG. 6 is a schematic diagram of a portion of a pixel array 600 displayed by left eye assembly 110 and right eye assembly 112. Similar to the arrangement of detector array 500, the pixel array 600 includes a plurality of pixels 602, including near-infrared pixels 604 and visible light pixels 606 arranged in a checkerboard pattern. In the exemplary embodiment, detector elements 502 correspond to pixels 602. As such, in the exemplary embodiment, to display different imaging modes on left eye assembly 110 and/or right eye assembly 112, different combinations of detector elements 602 are utilized such that different combinations of near-infrared pixels 604 and visible light pixels 606 and are displayed.

For example, when switch 116 (shown in FIG. 1) is set to a visible light imaging mode, visible light pixels 506 are used, and near-infrared pixels 504 are not used for imaging, such that visible light pixels 606 create a visible-light image. When switch 116 is set to a near-infrared imaging mode, near-infrared pixels 504 are used, and visible light pixels 506 are not used for imaging, such that near-infrared pixels 604 create a near-infrared image. Finally, in a hybrid imaging mode, both near-infrared detectors 504 and visible light detectors 506 are used for imaging, creating an image including near-infrared pixels 604 and visible light pixels 606. Filtering for the different imaging modes may be accomplished by a filter and/or polarizer (neither shown).

Figure 7A:
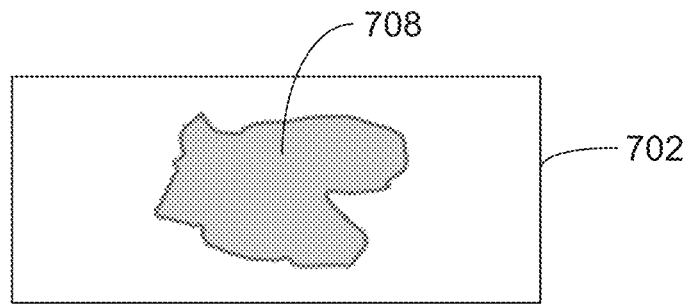
FIGS. 7A-7C are schematic depictions of images shown on the goggle device shown in FIG. 1.
Figure 7B:
Figure 7C:
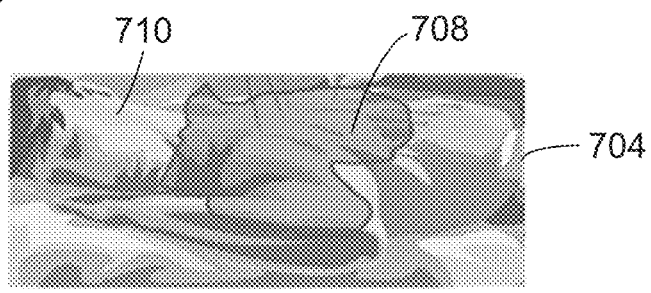

FIGS. 7A-7C are schematic diagrams of a near-infrared image 702, a visible light image 704, and a hybrid image 706, respectively, that may be displayed on goggle device 102 (shown in FIGS. 1 and 2). In near-infrared image 702, the molecular probe excited by near-infrared light source 122 (shown in FIG. 1) clearly delineates a tumor 708, but the rest of a subject 710 is not visible. In visible light image 704, subject 710 is visible, but tumor 708 is not visible. In hybrid image 706, however, both tumor 708 and subject 710 are visible. Accordingly, when user 104 views hybrid image 706 on goggle device 102, both tumors 708 and subject 710 are visible, enabling user 104 to better perform a surgical operation.

Figure 8A:
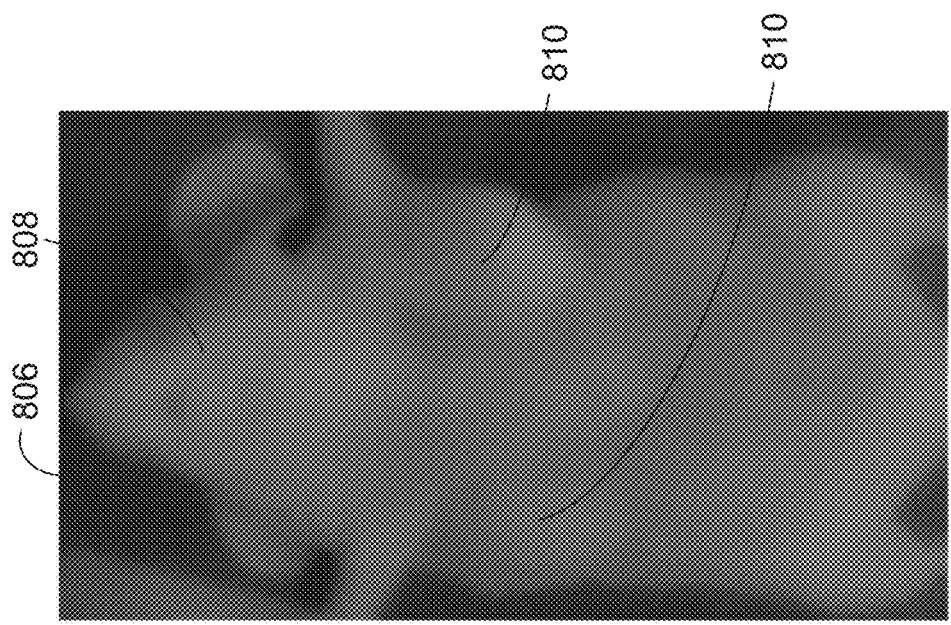
FIGS. 8A-8C are images shown on the display of the goggle device shown in FIG. 1.
Figure 8B:
Figure 8C:
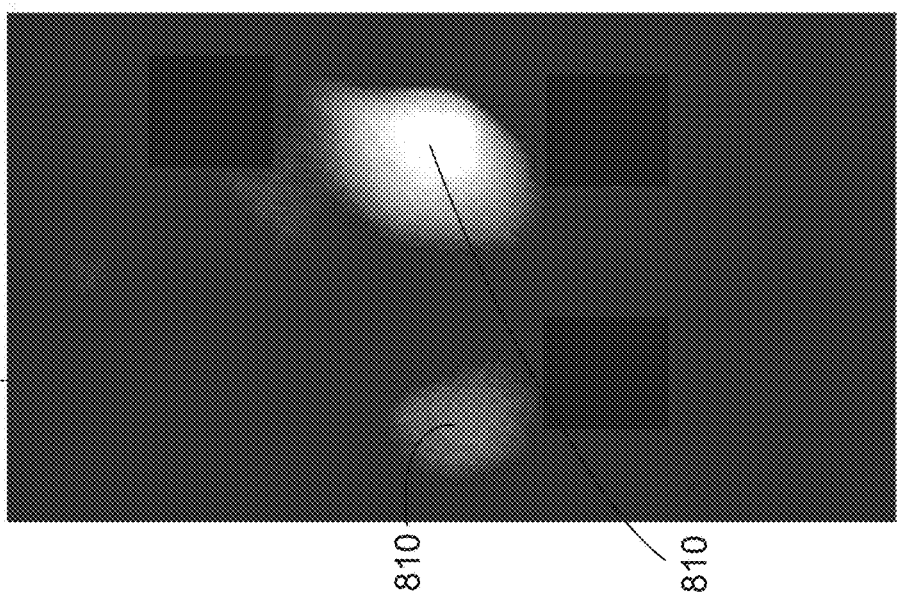

FIGS. 8A-8C are a near-infrared image 802, a visible light image 804, and a hybrid image 806, respectively, of a mouse 808 with tumors 810. In near-infrared image 802, the tumors 810 are visible, but the rest of mouse 808 is not visible. In visible light image 804, mouse 808 is visible, but tumors 810 are not visible. In hybrid image 806, however, both tumors 810 and mouse 808 are visible. Notably, using communications module 130 (shown in FIG. 2), images 802, 804, and/or 806 may also be viewed on computing device 108 (shown in FIG. 1).

Figure 9:
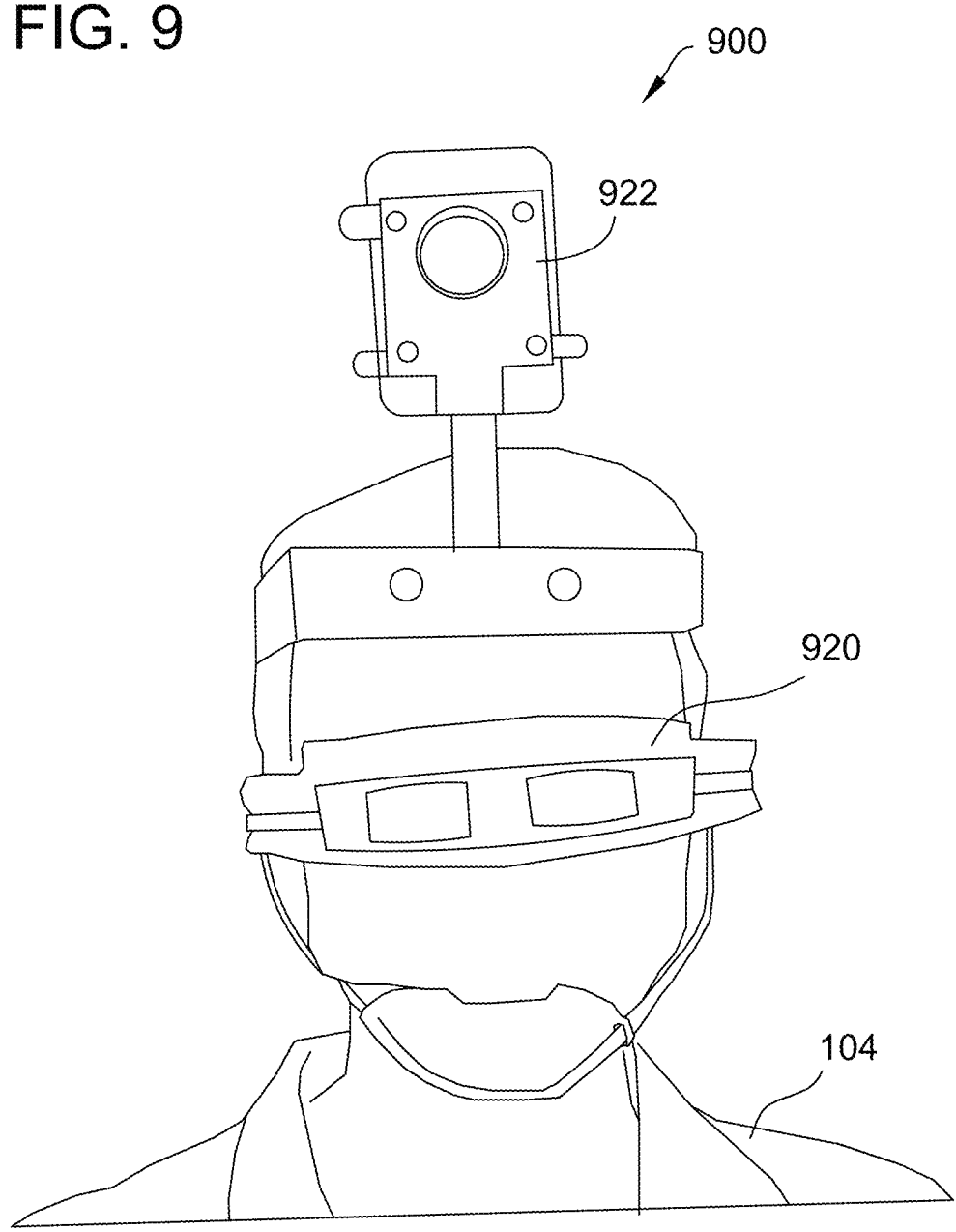
FIG. 9 is an image of an alternative goggle device.
Figure 10:
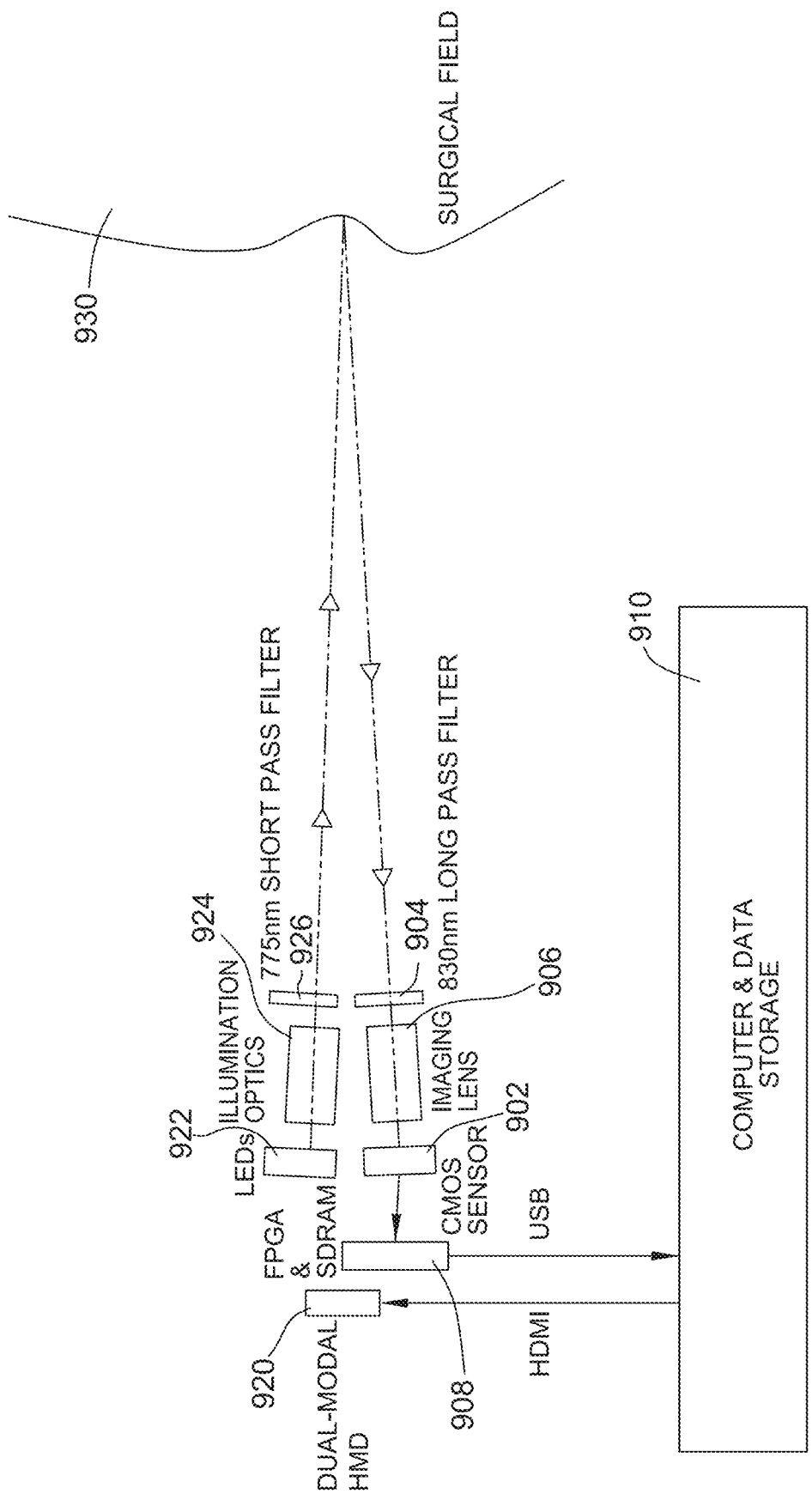
FIG. 10 is a block diagram of the goggle device shown in FIG. 9.

FIG. 9 is an image of an alternative goggle device 900 that may be used with goggle system 100 (shown in FIG. 1). FIG. 10 is a block diagram of the goggle device 900 shown in FIG. 9. In the exemplary embodiment, goggle device 900 is a head-mounted display (HMD) capable of fast temporal resolution and switching between an optical see-through mode and a video see-through mode. In the optical see-through mode, user 104 sees the real world through half-transparent mirrors, and the half-transparent mirrors are also used to reflect computer-generated images into the eyes of user 104, combining real and virtual world views. In the video see-through mode, cameras (or other suitable detection devices) capture the real-world view, and computer-generated images are electronically combined with the video representation of the real world view. As both the real and virtual world images are digital in the video see-through mode, lag between the real and virtual world images can be reduced. In the optical see-through mode, user 104 can visualize surroundings with natural vision. In the video see-through mode, real-time NIR fluorescence video is presented to user 104 with relatively high contrast. Allowing user 104 to switch between optical and video see-through modes simplifies surgical operations and allows user 104 to visualize subject 106 with natural vision or enhanced vision as desired.

Goggle device 900 includes a complementary metal-oxide-semiconductor (CMOS) imaging sensor 902 integrated onto a custom printed circuit board (PCB) platform (not shown). Alternatively, goggle device 900 may include a charge-coupled device (CCD) imaging sensor. A long-pass filter 904 is mounted on an objective imaging lens 906. In the exemplary embodiment, long-pass filter 904 is an 830 nanometer (nm) filter.

A control module 908 interfaces between CMOS imaging sensor 902 and a computing device 910, such as computing device 108. In the exemplary embodiment, control module 908 includes a field-programmable gate array (FPGA) integration model with a universal serial bus (USB) communication capabilities and a laptop computer. Data received by CMOS imaging sensor 902 is read out in multiple stages. In the exemplary embodiment, data from CMOS imaging sensor 902 is read out via a state machine implemented on the FPGA, and the data is stored in a first in first out (FIFO) process and transferred to a first synchronous dynamic random-access memory (SDRAM) chip in control module 908. In the exemplary embodiment, control module 908 includes two SDRAM chips, such that a first SDRAM chip stores pixel data from CMOS imaging sensor 902, while a second SDRAM chip transfers the data to an output FIFO on the FPGA for transferring the data to computing device 910 via a universal serial bus (USB). In some embodiments, control module 908 may include a data compression chip for compressing the data.

To display information to user 104, goggle device 900 includes an HMD unit 920 that interfaces with computing device 910 via a high-definition multimedia interface (HDMI) link to display real-time images on HMD unit 920. Goggle device 900 further includes and NIR light source 922 that emits NIR light through illumination optics 924 and a short-pass filter 926 to illuminate fluorescent molecular probes (such as indocyanine green dye) in a surgical field 930. Surgical field 930 may be, for example, a portion of subject 106 (shown in FIG. 1). In the exemplary embodiment, NIR light source 922 includes four NIR LEDs, and short-pass filter 926 is a 775 nm filter.

A sensitivity of goggle device 900 to detect a fluorescence signal from surgical field 930 is characterized using a signal-to-noise ratio (SNR), which compares a level of the desired signal relative to a noise level. Pixel binning and temporal averaging may be used to improve SNR of goggle device 900. Pixel binning involves combining signals from a group of pixels in a spatial domain, which is analogous to increasing the number of photons that contribute to the detected signal Binning improves the SNR estimate by the square root of the number of pixels binned. For instance, binning a neighborhood of 2 by 2 pixels improves the SNR by a factor of 2. However, improvement in SNR due to binning occurs at the expense of reduced spatial resolution and loss of high spatial frequency components in a final image.

Temporal averaging involves combing signals from a group of pixels in a time domain, which, like binning, is also analogous to increasing the number of photons that contribute to the detected signal. Temporal averaging increases SNR by the square root of the number of averaged pixels in the time domain. Hence, temporal averaging of four consecutive frames will increase SNR by a factor of 2. However, temporal averaging may create image lag when a moving target is imaged.

Both temporal averaging and pixel binning may be combined together to further improve SNR. For example, averaging 4 frames as well as averaging a pixel neighborhood of 2 by 2 pixels will improve SNR by a factor of 4 while reducing spatial and temporal resolution by a factor of 4. It was determined experimentally that SNR increases linearly with exposure time at a rate that depends on the concentration of a fluorescent molecular probe (e.g., indocyanine green dye). As the exposure time increases, SNR increases at the cost of a slower frame rate. Using goggle device 900 experimentally, sentinel lymph node mapping was performed on rats using NIR quantum dots (QDs), and fluorescence-guided liver surgery and intraoperative imaging were performed on mice. Goggle device 900 is capable of real-time fluorescence imaging of up to 60 frames per second (fps). Experimentally, it was determined that goggle device 900 detects fluorescence signals as low as 300 picomolar (pM) of indocyanine green dye. Compared to a charge-coupled device (CCD) imaging sensor, which has 20% quantum efficiency at 830 nm, CMOS imaging sensor 902 has a quantum efficiency of greater than 30% at 830 nm. Further, in the exemplary embodiment, goggle device 900 includes one or more buttons and/or switches (neither shown) for user 104 to select automatic or manual gain and automatic or manual exposure time.

Figure 11:
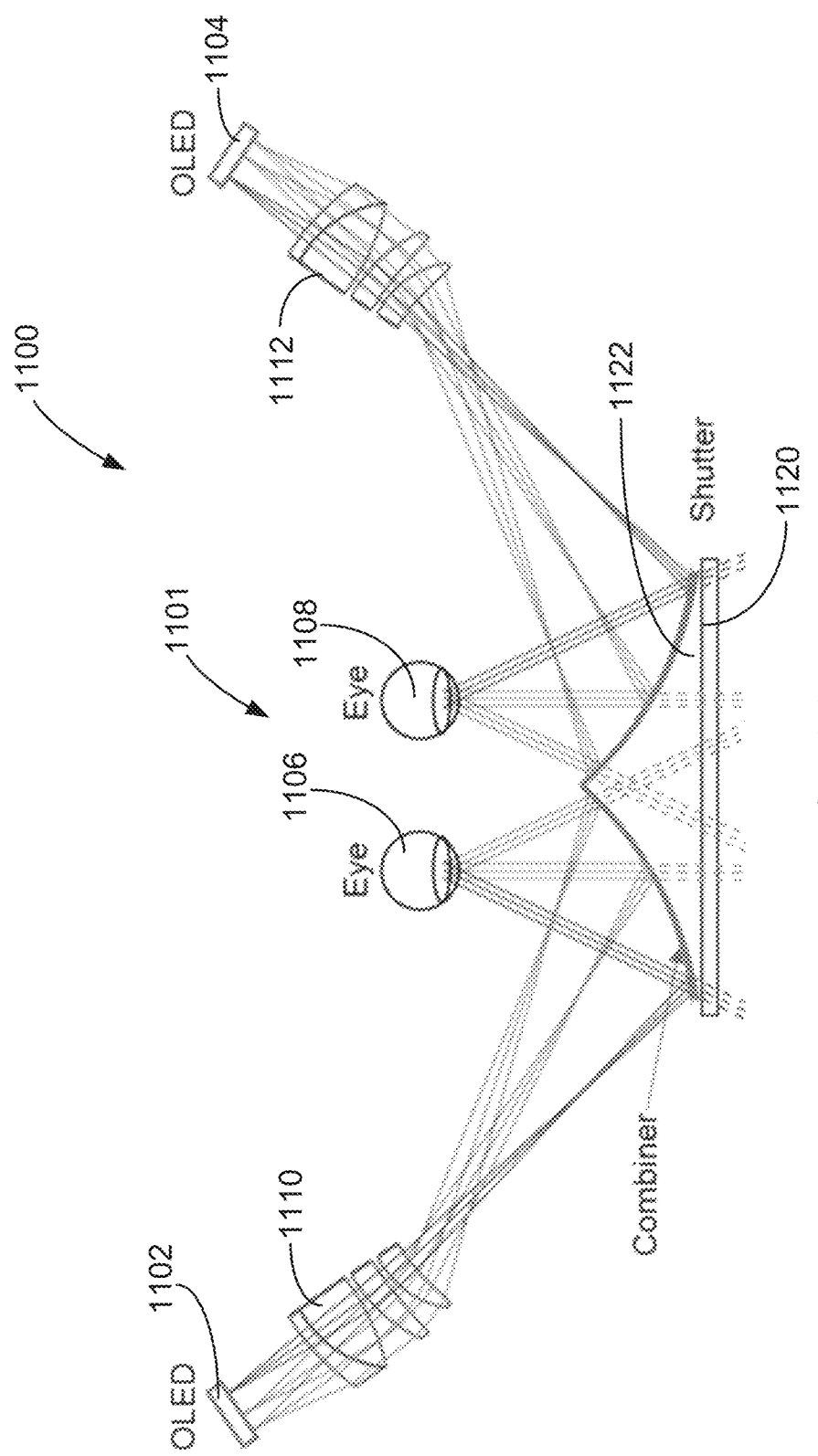
FIG. 11 is a schematic diagram of a display module of an alternative goggle device.

FIG. 11 is a schematic diagram of a display module 1101 for an alternative goggle device 1100 that may be used with goggle system 100 (shown in FIG. 1). Similar to goggle device 900, goggle device 1100 is implemented in a dual-mode visual and optical see-through HMD. However, unlike goggle device 900, goggle device 1100 provides three-dimensional (3D) imaging and display, as described herein. In one embodiment, a field of view for illumination and imaging of goggle device 1100 is 300 mm×240 mm at a distance between goggle device 1100 and subject 106 of 0.3 m-1.2 m.

Display module 1101 of goggle device 1100 includes a first organic light-emitting diode (OLED) 1102 and a second OLED 1104 to display images to a right eye 1106 and left eye 1108, respectively of user 104. First OLED 1102 emits light through a first optical assembly (e.g., imaging and/or focusing lenses) 1110, and second OLED 1104 emits light through a second optical assembly 1112.

OLED display technology provides benefits over liquid crystal display (LCD) technology as it uses approximately 80% less power than LCDs, has a nominal viewing area of approximately 160° (approximately 265% larger than LCDs), a nominal contrast ration of 10,000:1 (as compared to 60:1 for LCDs), and a significantly faster refresh rate, reducing eye fatigue and headaches. The OLED microdisplay is also more compact than its LCD counterpart because no additional illumination is needed. The proposed field of view of the display is 45°×36° with a microdisplay resolution of 1280×1024 (SXGA). In the exemplary embodiment, the pupil size of the goggle device 1100 is 10 mm in diameter. Off-axis design with aspherical plastic elements may be used to reduce the size and weight of goggle device 1100.

To switch between optical and video see-through modes, goggle device 1100 includes a fast liquid crystal shutter 1120 positioned in front of a combiner 1122. In the exemplary embodiment, combiner 1122 is a plastic element with 50% reflection on an inner (i.e., eye-facing) surface such that user 104 can see through combiner 1122 in optical see-through mode, and information from OLEDs 1102 and 1104 can be directed to user 104 in both modes.

When an external voltage is applied, fast liquid crystal shutter 1120 is transparent and transmits light. Without an external voltage, fast liquid crystal shutter 1120 blocks light from the surgical field and environment. Therefore, the goggle device 1110 can be switched between optical and video see-through modes easily and rapidly. In some embodiments, a switch (not shown) may be controlled by a foot paddle to enable hands-free operation. Using the video-see-through mode of goggle device 1100, 3D reflectance images and fluorescence images can be registered and presented precisely. The 3D fluorescence images can also be viewed with the optical-see-through mode, while user 104 views the surrounding environment naturally.

Figure 12:
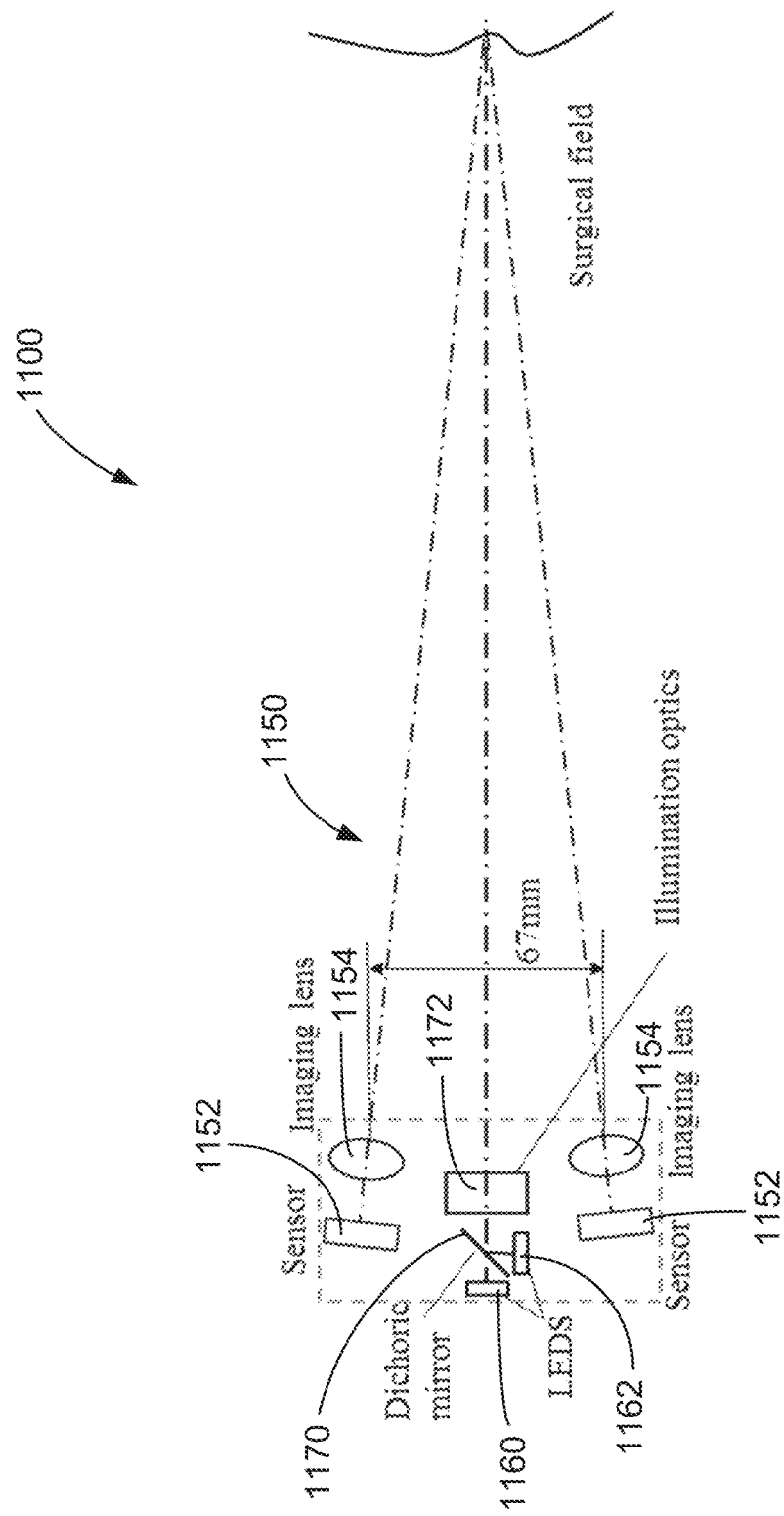
FIG. 12 is a schematic diagram of an imaging and illumination module that may be used with the alternative goggle device shown in FIG. 11.

FIG. 12 is a schematic diagram of an imaging and illumination module 1150 for goggle device 1100. For true stereoscopic vision, imaging and illumination module 1150 includes two separate and identical imaging systems and one illumination system between and above the imaging systems that provide uniform NIR illumination to excite fluorescent molecular probes and visible light illumination for reflectance imaging. Each of the two imaging systems includes a CMOS detector 1152 and an imaging lens 1154 in the exemplary embodiment. CMOS detectors 1152 provide higher resolution and faster frame rates than CCD detectors. In the exemplary embodiment, the distance between the imaging systems is 67 mm (the average inter-pupillary distance for adults).

As shown in FIG. 12, to provide a well-defined and uniform illumination region, the illumination system includes a first LED array 1160 and a second LED array 1162. In the exemplary embodiment, first LED array 1160 is a high power 780 nm LED array that includes 60 diode chips and optical output power of 4 Watts (W), and second LED array 1162 is a high power white light LED array that includes 16 diode chips to provide uniform illumination over an area of 300×240 mm. The power of NIR excitation is approximately 3 mW/cm$^2$ in the exemplary embodiment.

Light from first and second LED arrays 1160 and 1162 is combined using a dichroic mirror 1170 such that the illumination area from both first and second LED arrays 1160 and 1162 overlaps. The combined light is distributed using illumination optics 1172. Illumination optics 1172, in the exemplary embodiment, include freeform plastic lenses (not shown) that generate uniform light distribution and an excitation filter (not shown) that blocks excitation light over 800 nm.

Each CMOS detector 1152 and imaging lens 1154 capture white light reflectance and NIR fluorescence images simultaneously. In the exemplary embodiment, each CMOS detector 1152 includes a sensor of vertically-stacked photodiodes and pixelated NIR/visible spectrum filters. More specifically, in the exemplary embodiment, CMOS detector 1152 includes an array of 2268×1512 imaging pixels, and each pixel includes three vertically-stacked photodiodes that can separate spectra of blue, green, and red-NIR light for color imaging. As each pixel includes three vertically-stacked diodes, unlike at least some known imaging systems, there is no need to interpolate between neighboring pixels. Experimentation suggests that the quantum efficiency of the vertically-stacked photodiode sensor is approximately 35% at 800 nm, which is significantly better than at least some known CCD sensors and ideal for NIR imaging. The scanning rate of CMOS detector 1152 may be as fast as 40 fps, and a subset of the pixel array can be read out at higher frame rates (e.g., 550 fps for 128×128 pixels).

Figure 13:
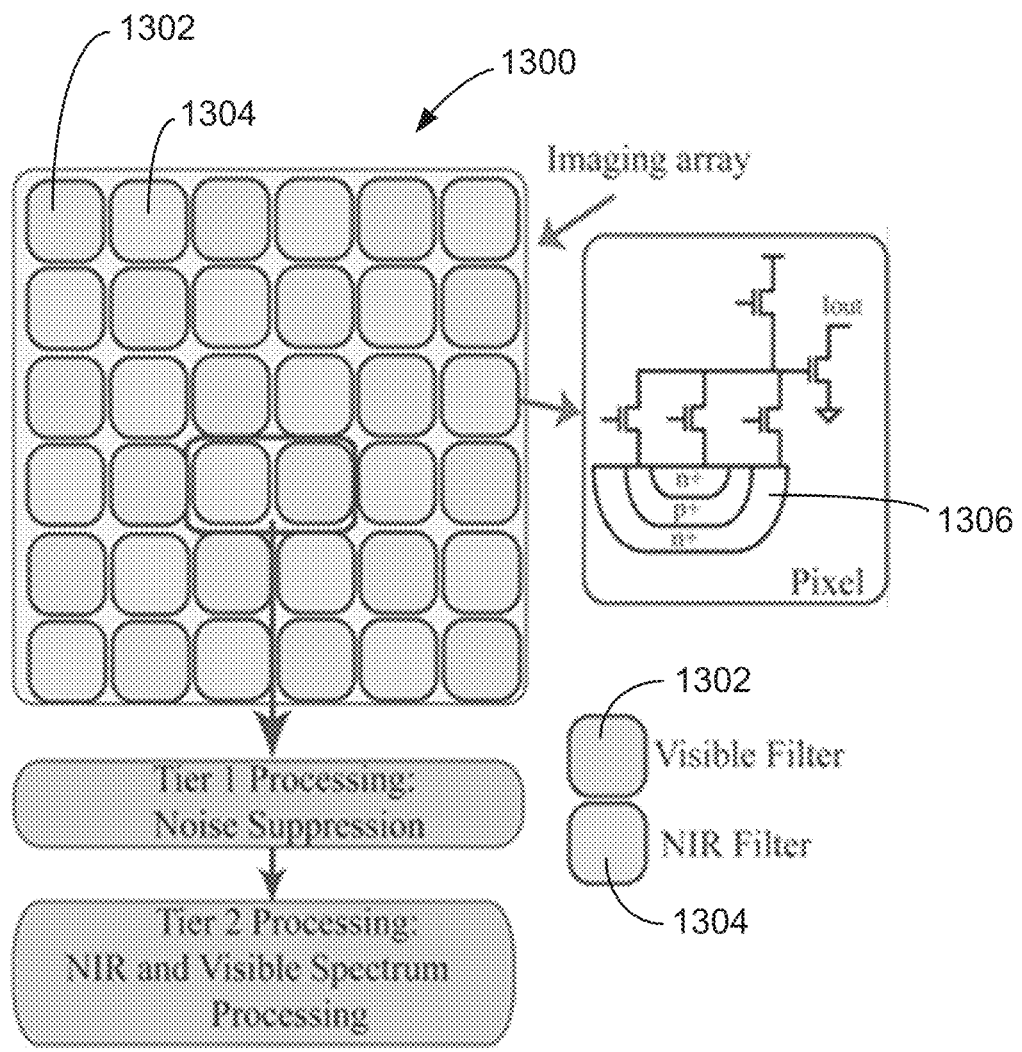
FIG. 13 is a schematic diagram of a filter array that may be used with the imaging and illumination module shown in FIG. 12.

FIG. 13 is a schematic diagram of a filter array 1300 that may be used with CMOS detector 1152 (shown in FIG. 12). Filter array 1300 alternates between pixels with a visible spectrum filter 1302 and pixels with a NIR filter 1304. Filter array 1300 may be created by taking a NIR filter the size of the entire array 1300 and selectively removing portions using a focus ion beam (FIB). Visible filters 1302, which are then selectively removed parts of the larger NIR filter, will allow passage of visible spectrum light, which will be subsequently absorbed by the vertically-stacked photodiodes 1306 for color separation.

Thus, white light reflectance imaging can be achieved with visible pixels. On the other hand, NIR filters 1304 will only allow NIR light of interest ($\lambda$>820 nm) to pass, and the NIR signal will be read out from the deepest of vertically-stacked photodiodes 1306. Due to the net effect of both spectrum separation mechanisms (NIR filter 1304 and vertically-stacked photodiodes 1306), the performance of NIR fluorescence detection will be further enhanced compared to the conventional method of using a NIR filter alone. The CMOS detector 1152 enables co-registration of color images and NIR images on-chip while reducing the number of sensors required for 3D reflectance/fluorescence imaging. This facilitates eliminating artifacts in co-registration due to motion and minimizes the delay due to exhausting off-chip computation.

Goggle device 1100 includes an autofocus feature without moving parts that optimizes a focus in the exemplary embodiment. A zoom lens with a compact piezo actuator or a liquid lens with a variable, voltage-dependent focal length may be used to implement the autofocus feature. In the exemplary embodiment, image processing for goggle device 1100 is performed by an FPGA coupled to CMOS detectors 1152 and OLEDs 1102 and 1104.

The goggle devices described herein may be used with or without contrast agents. In the absence of extrinsic contrast agents, imaging signals for endogenous fluorophores or biomolecules may be used to provide imaging contrast. At least some embodiments utilize NIR fluorescent or luminescent molecules or materials that localize selectively in a tissue of interest. As noted above, indocyanine green dye may be used as a fluorescent molecular probe with the goggle devices described herein. Other fluorescent dyes such as NIR pyrrolopyrrole cyanine dyes or luminescent materials such as quantum dots or dye-loaded nanoparticles may be utilized. However, uptake of high-affinity probes in small tumor cells may be overwhelmed by background fluorescence from normal tissue, decreasing contrast between tumor cells and background tissue. Instead, the fluorescent molecules such as dyes, or materials such as luminescent nanoparticles, could be linked to another molecule or group of molecules that will improve selective uptake in the tissues or cells of interest. For example, fluorescent molecular probes that bind selectively to protein receptors or other biomarkers overexpressed in tumor cells or target tissue may also be utilized with the goggle devices described herein.

Figure 14A:
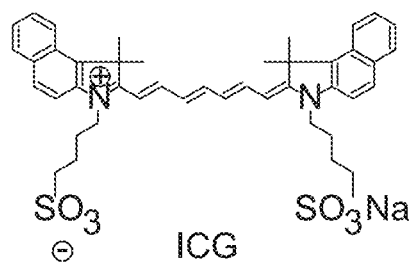
FIGS. 14A-14D are exemplary fluorescent molecular probes.
Figure 14B:
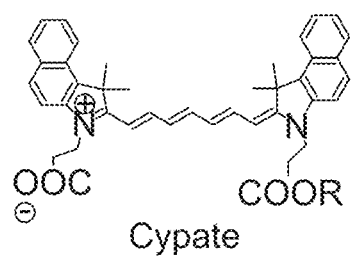
Figure 14C:
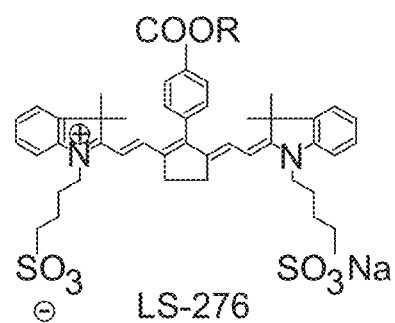
Figure 14D:
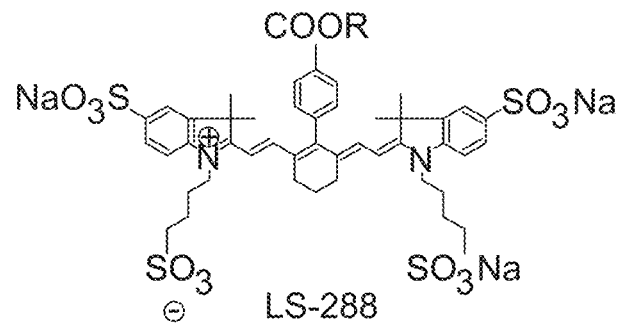

FIGS. 14A-14D are a plurality of exemplary fluorescent molecular probes. FIG. 14A shows indocyanine green dye. Cypate, shown in FIG. 14B, is a NIR cyanine dye with similar spectral properties to indocyanine green dye. Cypate, LS-276, shown in FIG. 14C, and LS-288, shown in FIG. 14D, are models of hydrophobic, intermediate hydrophilic, and hydrophilic dyes, respectively.

An example of a tumor-targeted molecular probe is LS-301, which has the structure, Cypate-cyclo (D-Cys-Gly-Arg-Asp-Ser-Pro-Cys)-Lys-OH. The spectral properties of LS-301 are suitable for NIR imaging applications (e.g., excitation/emission 790/810 nm in 20% DMSO solution; fluorescence quantum yield ($\psi$) 0.1 referenced to ICG). The ABIR binding affinity for LS-301 is Ki=26.2±0.4 nM relative to reference cypate-labeled RGD peptide (Ki=1.2±0.7 nM). In addition to conferring tumor selectivity on LS-301, the unnatural D-cysteine on the peptide moiety confers higher stability because of its resistance to degradation by proteases. This biological stability in serum allows initial imaging and potential follow-up surgery to be conducted within 48 hours before subsequent hydrolysis of the probe through L-amino acid residues.

Experimentally, NIR fluorescence microscopy of LS-301 in diverse tumor cells showed punctate intracellular fluorescence typical of receptor-mediated endocytosis and barely visible uptake in non-tumor cells. This uptake was successfully inhibited with unlabeled cyclic (RGDFV) reference peptide in A549 tumor cells, demonstrating the versatility of the imaging probe in detecting tumors relative to non-tumor cells.

Hydrophobic dyes, such as cypate, bind to albumin and other proteins. The high binding constant decreases their bioavailability for the target tumors and prolongs the blood circulation time, thereby increasing background fluorescence at early imaging time points. In contrast, more hydrophilic dyes and their peptide conjugates rapidly extravasate into tissues, quickly removing the probe from circulation. Although the hydrophilic probes are suitable for image-guided surgery because of the fast clearance, the contrast between tumor and surrounding tissue also depends on having sufficient time for molecular interaction between the target tumor proteins and the molecular probe. Thus, the low background signal obtained may be offset by the low signal at the tumor site. Experimental data suggest that LS-276 dye (shown in FIG. 14C) will bridge the gap between rapid and delayed blood clearance, which affects the bioavailability of the probes to a target tissue.

Figure 15:
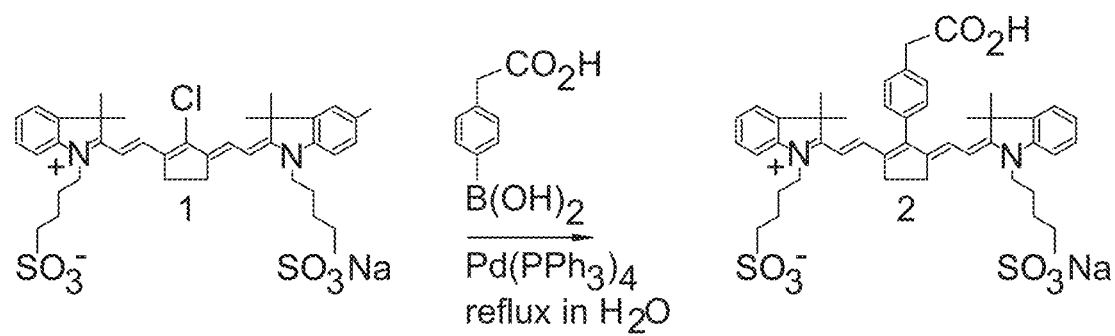
FIG. 15 is a schematic diagram of an exemplary synthesis for an LS-301 fluorescent molecular probe.

Due to a direct linkage of a carboxylic acid with a phenyl group in LS-276, LS-276 may have relatively low reactivity with peptides and proteins, resulting in multiple side products that are difficult to remove. Accordingly, in some embodiments, a fluorophore based on a benzyl instead of the current phenyl carboxylic acid used for LS-276 may be utilized. Since the pure compound is a solid, re-crystallization methods may be used where ethyl acetate and chloroform mixtures are used to precipitate the dye in >99% HPLC/HRMS purity. FIG. 15 is a schematic diagram of the synthesis of reactive benzylcarboxylic acid for solid-phase labeling of LS-301 peptide. Using this derivative of LS-276 may double the quantum yield of cypate used in LS-301. In some embodiments, the method may produce the desired compound in high yield (>70%) and purity (>99%). The method is also scalable, with the potential to produce up to 10 grams of compound.

In some embodiments, the LS-301 peptide may be slightly altered to assess further improvements in tumor selectivity (e.g., cyclo(DCys-Gly-Arg-Asp-Ser-Pro-DCys)-Lys-OH, cyclo(Cys-Gly-Arg-Asp-Ser-Pro-Cys)-Lys-OH, cyclo(Cys-Arg-Gly-Asp-Ser-Pro-Cys)-Lys-OH, cyclo(DCys-Arg-Gly-Asp-Ser-Pro-Cys)-Lys-OH, and cyclo(DCys-Arg-Gly-Asp-Ser-Pro-DCys)-Lys-OH). These peptides are labeled with dye 2 at the N-terminus.

The goggle devices and fluorescent probes described herein may be implemented in a plurality of surgical settings, including, but not limited to, detecting tumors related to breast cancer in mice, adenocarcinoma in canines, and hepatocellular carcinoma (HCC) in humans.

The goggle devices and fluorescent probes described herein assist in identifying tumor boundaries and performing biopsies. The goggle devices and fluorescent probes described herein are also applicable to other surgical interventions such as cardiac surgery and assessing wound healing.

In one example, goggle device 102 (shown in FIG. 1) and the fluorescent probe LS-301 described herein were utilized in mapping positive lymph nodes (PLNs) in mice. Based on the information provided by non-invasive fluorescence imaging using goggle device 102 and LS-301, regions of interest that might contain PLNs were explored and examined PLNs were identified and resected under image guidance. The presence of cancerous tissue in the PLNs was confirmed by bioluminescence imaging. This verifies the feasibility of the non-invasive fluorescence imaging, allowing clinicians to rapidly stage cancer non-invasively. Using goggle device 102 and fluorescent probe LS-301 non-invasively can provide a first-line screening that provides general information in an operating room in real-time. Further, the fluorescence signals monitored in PLNs might be used as an indicator of the efficacy of treatment regimens such as radiotherapy, chemotherapy, and targeted therapy.

In another example, a multimodal detection technique was implemented in which goggle-aided fluorescence imaging (e.g., using goggle device 102 (shown in FIG. 1) and indocyanine green dye) was combined with ultrasound imaging and standard histology. Specifically, fluorescence imaging was used to detect liver tumors in mice and to perform liver resections on the tumors. In addition to single tumors, scattered satellite lesions were also detected. Further, liver resection was performed on a rabbit using ultrasound, fluorescence imaging, and standard histology. The presence of tumors in the rabbit was confirmed by ultrasound and then observed in real-time using fluorescence goggle system 100 (shown in FIG. 1). The excised tissues were later examined by histopathology, and it was confirmed that the tumors were cancerous.

In another example, goggle device 102 (shown in FIG. 1) and indocyanine green dye were used to image hepatocellular carcinoma (HCC) in human patients. Both intravenous and transarterial hepatic (TAH) delivery of indocyanine green dye were used. Primary tumors and satellite tumors were both detected using fluorescence imaging, some of which were not identified in pre-operative MRI and CT images or by visual inspection and palpation. Histologic validation was used to confirm HCC in the patients. The HCC-to-liver fluorescence contrast detected by goggle device 102 was significantly higher in patients that received TAH delivery instead of intravenous delivery.

The systems and methods described herein provide a goggle device in communication with a computing device. The goggle device enables a user to view a subject in a plurality of imaging modes in real-time. The imaging modes include a hybrid-imaging mode that simultaneously captures and displays pixels of image data of a first imaging mode and pixels of image data of a second imaging mode. Accordingly, a user is able to quickly and easily visualize a subject during a surgical operation.

Notably, the goggle system and goggle device described herein may be utilized in a broad variety of medical applications, including small animal imaging, veterinary medicine, human clinical applications, endoscopic applications, laparoscopic applications, dental applications, cardiovascular imaging, imaging inflammations, wound healing, etc. Further, the goggle system and goggle device described herein may be used in other imaging applications outside of the medical field.

The order of execution or performance of the operations in the embodiments of the disclosure illustrated and described herein is not essential unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the disclosure, including the best mode, and also to enable any person skilled in the art to practice the disclosure, including making and using any devices or systems and performing any incorporated methods. The patentable scope of the disclosure is defined by the claims and may include other examples that occur to those skilled in the art. Such other examples are intended to be within the scope of the claims if they have structural elements that do not differ from the literal language of the claims or if they include equivalent structural elements with insubstantial differences from the literal language of the claims.

The invention claimed is:

1. A device, comprising:
   a detector configured to simultaneously acquire image data from a plurality of fluorescent molecules, a plurality of luminescent materials, or a combination thereof in a state of excitation caused by a fluorescence excitation light source, and from visible light illuminated by a white light source; and
   at least one display module configured to display pixels of the acquired image data in real-time.

2. The device of claim 1, wherein the white light source comprises a plurality of white light emitting diodes.

3. The device of claim 1, further comprising a second fluorescence excitation light source.

4. The device of claim 1, wherein the at least one display module is further configured to display an image chosen from a first image mode associated with the image data from the plurality of fluorescent molecules, the plurality of luminescent materials, or a combination thereof, and a second image mode associated with the image data from the visible light.

5. The device of claim 1, wherein the at least one display module comprises at least one eye assembly.

6. The device of claim 1, further comprising an endoscope.

7. The device of claim 6 adapted for laparoscopic applications.

8. The device of claim 4, wherein the first image mode is a near-infrared image mode.

9. The device of claim 1, further comprising a switch configured to switch between different imaging modes displayed in real-time on the at least one display module.

10. The device of claim 1, wherein the plurality of luminescent materials is localized in a tissue of interest, and the fluorescence emitted by the excited plurality of luminescent materials is absorbed by the plurality of fluorescent molecules.

11. The device of claim 1, wherein the plurality of fluorescent molecules, the plurality of luminescent materials, or the combination thereof comprises a fluorescent molecular probe chosen from LS-301.

12. A system comprising:
   a computing device;
   a detector configured to simultaneously acquire image data from a plurality of fluorescent molecules, a plurality of luminescent materials, or a combination thereof in a state of excitation caused by a fluorescence excitation light source, and from visible light illuminated by a white light source; and
   at least display module configured to display pixels of the acquired image data in real-time.

13. The system of claim 12, wherein the white light source comprises a plurality of white light emitting diodes.

14. The system of claim 12, further comprising a second fluorescence excitation light source.

15. The system of claim 12, wherein the at least one display module is further configured to display an image chosen from a first image mode associated with the image data from the plurality of fluorescent molecules, the plurality of luminescent materials, or a combination thereof, and a second image mode associated with the image data from the visible light.

16. The system of claim 12, further comprising an endoscope.

17. The system of claim 16 adapted for laparoscopic applications.

18. A method for detection using a device, the method comprising:
   acquiring image data with a device of claim 1 from a subject, the image data being acquired from a plurality of fluorescent molecules, a plurality of luminescent materials, or a combination thereof in a state of excitation caused by a fluorescence excitation light source, and from visible light illuminated by a white light source; and
   displaying pixels of the acquired image data from the subject in real-time on the at least one display module of the device.

19. The method of claim 18, further comprising administering the plurality of fluorescent molecules, the plurality of luminescent materials, or the combination thereof to a subject.

20. The method of claim 19, wherein the plurality of fluorescent molecules, the plurality of luminescent materials, or the combination thereof comprises a fluorescent molecular probe chosen from LS-301.

\* \* \* \* \*